United States Patent
Walker et al.

(10) Patent No.: US 10,962,508 B2
(45) Date of Patent: Mar. 30, 2021

(54) ULTRASOUND-BASED METHOD AND RELATED SYSTEM TO EVALUATE HEMOSTATIC FUNCTION OF WHOLE BLOOD

(75) Inventors: William F. Walker, Earlysville, VA (US); Francesco Viola, Charlottesville, VA (US); F. William Mauldin, II, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 763 days.

(21) Appl. No.: 13/496,349

(22) PCT Filed: Sep. 17, 2010

(86) PCT No.: PCT/US2010/049342
§ 371 (c)(1),
(2), (4) Date: May 30, 2012

(87) PCT Pub. No.: WO2011/035162
PCT Pub. Date: Mar. 24, 2011

(65) Prior Publication Data
US 2012/0244564 A1  Sep. 27, 2012

Related U.S. Application Data

(60) Provisional application No. 61/243,335, filed on Sep. 17, 2009.

(51) Int. Cl.
*G01N 29/02* (2006.01)
*G01N 29/34* (2006.01)
(Continued)

(52) U.S. Cl.
CPC ......... *G01N 29/343* (2013.01); *G01N 29/024* (2013.01); *G01N 29/032* (2013.01);
(Continued)

(58) Field of Classification Search
CPC .............. G01N 29/032; G01N 29/343; G01N 2291/044; G01N 2291/02466; G01N 2291/02827
(Continued)

(56) References Cited

U.S. PATENT DOCUMENTS 5,487,387 A    1/1996  Trahey et al.
5,673,699 A   10/1997  Trahey et al.
(Continued)

FOREIGN PATENT DOCUMENTS

AU   2010295484 B2   3/2014
CN   102753967 A    10/2012
WO   WO-2011035162 A1   3/2011

OTHER PUBLICATIONS

"U.S. Appl. No. 12/940,838, Notice of Allowance dated May 30, 2013", 13 pgs.
(Continued)

*Primary Examiner* — Rebecca M Fritchman
(74) *Attorney, Agent, or Firm* — Schwegman Lundberg & Woessner, P.A.

(57) ABSTRACT

Method and systems for of evaluating a mechanical property of a material by applying force to the material sufficient to physically displace a portion of the material, measuring displacement of the material, adaptively adjusting the force when the displacement measured is not within a predetermined range of displacement values, wherein the force is increased or decreased depending upon whether the measured displacement is below or above the predetermined range, respectively, and computing a mechanical property value resultant from the displacement of the material.

22 Claims, 15 Drawing Sheets

(51) Int. Cl.
G01N 29/032 (2006.01)
G01N 29/44 (2006.01)
G01N 33/49 (2006.01)
G01N 29/024 (2006.01)
C12M 1/42 (2006.01)

(52) U.S. Cl.
CPC ......... *G01N 29/34* (2013.01); *G01N 29/4472* (2013.01); *G01N 33/4905* (2013.01); *G01N 2291/025* (2013.01); *G01N 2291/02466* (2013.01); *G01N 2291/02827* (2013.01); *G01N 2291/044* (2013.01)

(58) Field of Classification Search
USPC .................................................. 435/13, 287.1
See application file for complete search history.

(56) References Cited

U.S. PATENT DOCUMENTS

| | | | |
|---|---|---|---|
| 5,903,516 A | 5/1999 | Greenleaf et al. | |
| 5,921,928 A | 7/1999 | Greenleaf et al. | |
| 5,991,239 A | 11/1999 | Fatemi-Booshehri et al. | |
| 6,039,691 A | 3/2000 | Walker et al. | |
| 6,371,912 B1 | 4/2002 | Nightingale et al. | |
| 6,692,439 B1 | 2/2004 | Walker et al. | |
| 7,699,776 B2 | 4/2010 | Walker et al. | |
| 7,713,201 B2 | 5/2010 | Chen et al. | |
| 7,750,537 B2 | 7/2010 | Hossack et al. | |
| 8,548,759 B2 | 10/2013 | Walker et al. | |
| 2003/0013958 A1 | 1/2003 | Govari et al. | |
| 2003/0105398 A1* | 6/2003 | Vitek ............................ | 600/437 |
| 2005/0004463 A1 | 1/2005 | Chen et al. | |
| 2005/0015001 A1 | 1/2005 | Lec et al. | |
| 2005/0148899 A1* | 7/2005 | Walker et al. ................. | 600/553 |
| 2005/0154303 A1 | 7/2005 | Walker et al. | |
| 2006/0052697 A1 | 3/2006 | Hossack et al. | |
| 2006/0100516 A1 | 5/2006 | Hossack et al. | |
| 2007/0016022 A1 | 1/2007 | Blalock et al. | |
| 2007/0016044 A1 | 1/2007 | Blalock et al. | |
| 2008/0091678 A1 | 4/2008 | Walker et al. | |
| 2008/0249408 A1* | 10/2008 | Palmeri et al. ................ | 600/438 |
| 2008/0302187 A1 | 12/2008 | Huber et al. | |
| 2009/0048519 A1 | 2/2009 | Hossack et al. | |
| 2009/0299184 A1 | 12/2009 | Walker et al. | |
| 2010/0063399 A1 | 3/2010 | Walker et al. | |
| 2010/0138163 A1* | 6/2010 | Gallippi ................. | A61B 8/485 702/19 |
| 2010/0142781 A1 | 6/2010 | Walker et al. | |
| 2010/0168578 A1 | 7/2010 | Garson, Jr. | |
| 2010/0268086 A1 | 10/2010 | Walker et al. | |
| 2011/0137588 A1 | 6/2011 | Walker et al. | |

OTHER PUBLICATIONS

"Australian Application Serial No. 2010295484, First Examiner Report dated Aug. 27, 2013", 3 pgs.
"Australian Application Serial No. 2010295484, Response filed Feb. 19, 2014 to Office Action dated Aug. 27, 2013", 53 pgs.
"Canadian Application Serial No. 2,774,680, Voluntary Amendment dated Mar. 16, 2012", 6 pgs.
"Chinese Application Serial No. 201080052056.1, Office Action dated Jan. 2, 2014", With English Translation, 14 pgs.
"Chinese Application Serial No. 201080052056.1, Office Action dated Nov. 15, 2014", 8 pgs.
"International Application Serial No. PCT/US2010/049342, Search Report dated Nov. 16, 2010", 4 pgs.
"International Application Serial. No. PCT/US2010/049342, Written Opinion dated Nov. 16, 2010", 16 pgs.
"European Application Serial No. 10817919.3,Response filed Jun. 26, 2017 to Extended European Search Report dated Nov. 28, 2017", 48 pgs.
Kirkpatrick, John Paxton, "Dynamic Rheological Studies of Coagulation and Fibrinolysis", Kirkpatrick Thesis, (May 1979), 285 pgs.
"European Application Serial No. 10817919.3, Extended European Search Report dated Nov. 28, 2016", 9 pgs.
Burghardt, W R, et al., "Nonlinear Viscoelasticity and the Therombelastpgraph: I.Studies on Bovine Plasma Clots", Biorheology, Elsevier Science Ltd., Oxford, GB, vol. 32, No. 6,, (Jan. 1, 1995), 621-630.
Mauldin, F W, "Adaptive radiation force ultrasound for monitoring hemostasis in whole blood", Ultrasonics Symposium (IUS), 2009 IEEE International, IEEE, Piscataway, NJ, USA, (Sep. 20, 2019), 173-176.
"European Application Serial No. 10817919.3, Communication Pursuant to Article 94(3) EPC dated Mar. 31, 2020", 5 pgs.
"European Application Serial No. 10817919.3, Response Filed Aug. 7, 2020 to Communication Pursuant to Article 94(3) EPC dated Mar. 31, 2020", 21 pgs.
"European Application Serial No. 10817919.3, Voluntary Amendments filed on Apr. 17, 2012", 14 pgs.
"International Applicaiton Serial No. PCT/US2010/049342, International Preliminary Report on Patentability dated Mar. 29, 2012", 13 pgs.
Hsu, Stephen J, et al., "Challenges and Implementation of Radiation-Force Imaging with an Intracardiac Ultrasound Transducer", ieee transactions on ultrasonics, ferroelectrics, and frequency control, vol. 54, No. 5, May 2007, 996-1009.
Nightingale, et al., "Acoustic Radiation Force Impluse Imagin, In Vivo Demonstration of Clinical Feasibility", Ultrasound in Medicine & Biology, Preprint submitted to Ultrasound in Medicine and Biology, (Oct. 24, 2001), 21 pgs.
Nightingale, K R, et al., "Generation and Detection of Acoustic Streaming to Differentiate Between Solid and Cystic Breast Lesions", 1994 Ultrasonic Symposium, 1653-1656.
Nightingale, Kathryn R, et al., "A Finite Element Model of Remote Palpation of Breast Lesions Using Radiation Force: Factors Affecting Tissue Displacement", Ultrasonic Imaging 22, 35-54 (2000), (2000), 35-54.
Nightingale, Kathryn, et al., "Acoustic Radiation Force Impulse Imaging: Remote Palpation of the Mechanical Properties of Tissue", 2002 IEEE Ultrasonics Symposium, (2002), 1821-1830.
Nightingale, Kathryn R, et al., "On the feasibility of remote palpation using acoustic radiation force", J. Acoust. Soc. Am. 110 (1), Jul. 2001, (2001), 625-634.
Nightingale, Kathryn, et al., "Shear-Wave Generation Using Acoustic Radiation Force: In Vivo and Ex Vivo Results", Ultrasound in Med. & Biol., vol. 29, No. 12, pp. 1715-1723, 2003, (2003), 1715-1723.
Palmeri, Mark L, et al., "A Finite-Element Method Model of Soft Tissue Response to Impulsive Acoustic Radiation Force", IEEE Transactions on Ultrasonics, Ferroele(Jtrics, and Frequency Control, vol. 52, No. 10, Oct. 2005, (2005), 1699-1712.
Palmeri, Mark L, et al., "Ultrasonic Tracking of Acoustic Radiation Force-Induced Displacements in Homogeneous Media", ieee transactions on ultrasonics, ferroelectrics, and frequency control, vol. 53, No. 7, Jul. 2006, (2006), 1300-1313.
Tabilo-Munizaga, Gipsy, et al., "Rheology for the food industry", Journal of Food Engineering 67, (2005), 147-156.
Zhai, Liang, et al., "An Integrated Indenter-ARFI Imaging System for Tissue Stiffness Quantification", Ultrason Imaging. Apr. 2008 ; 30(2): 95-111., (2008), 24 pgs.

* cited by examiner

ULTRASOUND-BASED METHOD AND RELATED SYSTEM TO EVALUATE HEMOSTATIC FUNCTION OF WHOLE BLOOD

This application is a U.S. National Stage Filing under 35 U.S.C. 371 from International Patent Application Serial No. PCT/US2010/049342, filed on Sep. 17, 2010 and published on Mar. 24, 2011 as WO 2011/035162A1, which claims the benefit of priority of U.S. Provisional Patent Application Ser. No. 61/243,335, filed on Sep. 17, 2009, the contents of which are incorporated herein by reference.

GOVERNMENT RIGHTS

This invention was made with government support under federal grant no. EB005433 awarded by the National Institute of Health (NIH). The United States Government has certain rights in this invention.

BACKGROUND OF THE INVENTION

Unregulated hemostasis represents a leading cause of mortality and morbidity in the developed world. The ability to recognize and quantify defects of the hemostatic process is critical to reduce mortality and implement appropriate treatment.

The formation of a blood clot and its successive dissolution, referred to as the hemostatic process, is required to arrest blood loss from an injured vessel. This process is the result of a delicate functional balance between plasma coagulation factors, platelets, and fibrinolytic proteins. Each of these elements plays an important role in activating/deactivating the others, and the appropriate stimuli are necessary to prevent excessive blood loss without causing inappropriate thrombosis, see Laposata M., et al., *The Clinical Hemostasis Handbook*, Year Book Medical Publisher 1989. Disruption of this balance plays a significant role in the onset of potentially fatal conditions, including myocardial infarction, stroke, deep vein thrombosis, pulmonary embolism, and hemorrhage, see Hoyert et al., "Deaths: preliminary data for 2003", Natl. Vital Stat. Rep. 2005; 53:1-48 and Hambleton et al., "Coagulation: Consultative Hemostasis"; Hematology 2002; 1:335-352.

The hemostatic process is initiated by the activation and subsequent adhesion of platelets to the site of injury within the vessel wall. Activated platelets recruit other platelets and interact with fibrinogen in the blood plasma to form a platelet-plug that serves as the initial response to stop blood loss. Hemostasis then proceeds with a cascade of proteolytic reactions of the plasma coagulation proteins that ultimately form a three-dimensional network of fibrin that strengthens the platelet-plug. The fibrin chains are cross-linked and stabilized by the plasma factor XIIIa (FXIIIa). Platelets also have a central role in regulating the process of fibrin polymerization. The final step of hemostasis (i.e., fibrinolysis) involves the activation of the plasma protein plasmin, which lyses the blood clot when its useful life is over. This cell-based model of hemostasis closely reflects the in vivo physiological process, e.g., see Hoffman et al., "A cell-based model of hemostasis"; Thromb. Haemost. 2001; 85:958-965 and Becker, "Cell-Based Models of Coagulation: A Paradigm in Evolution"; J. Thromb. Thrombolysis 2005; 20:65-68.

The mechanical properties of blood clots are essential for its primary function of stopping blood loss. Alterations in clot structure and its underlying mechanical properties have been implicated in thrombotic disease and other life threatening pathologies, see Weisel, J. W., "Enigmas of Blood Clot Elasticity"; Science 2008; 320:456. Recently, it was shown that fibrin clots of patients affected by premature coronary artery disease have a different structure and higher stiffness compared to the fibrin clots of healthy age-matched controls, see Collet et al, "Altered Fibrin Architecture is Associated with Hypofibrinloysis and Premature Coronary Atherothrombosis"; Arterioscler. Thromb. Vase. Biol. 2006; 26:2567-2573. The mechanics of fibrin networks have been studied extensively at the macroscopic level see Ryan et al., "Structural Origins of Fibrin Clot Rheology"; Biophys. J. 1999; 77:2813-2826 and Jen et al., "The Structural Properties and Contractile Force of a Clot"; Cell Motil. 1982; 2:445-455. The viscoelastic properties of individual fibrin strands have also been investigated by means of AFM (see Liu et al., "Fibrin Fibers Have Extraordinary Extensibility and Elasticity"; Science 2006; 313:634) and "optical tweezers", see Collet et al., "The elasticity of an individual fibrin fiber in a clot"; Proc. Natl. Acad. Sci. USA 2005; 102:9133-9137. These studies, however, have not examined the combined effects of coagulation plasma factors, platelets, and fibrinolytic proteins. It would be desirable to provide systems and methods with the ability to monitor and characterize the mechanical properties of whole blood during clot formation and dissolution to: (i) enhance understanding of both normal and pathological hemostasis, (ii) identify patients at high risk of bleeding and thrombotic disorders, (iii) inform appropriate medical treatment, and (iv) support the development of new pharmacological agents.

Current tests of hemostasis can be divided into two broad categories: endpoint biochemical assays and mechanical/viscoelastic analyzers. Endpoint assays are traditionally performed on blood plasma and include such tests as the pro-thrombin time (PT), activated partial thromboplastin time (aPTT), and the activated clotting time (ACT). While each of these assays measures a different aspect of the coagulation cascade, even in combination they do not provide a complete representation of overall hemostasis, see Gravlee et al., "Predictive value of blood clotting tests in cardiac surgical patients"; Aim. Thorac. Surg. 1994; 58:216-221 and Bajaj et al., "New insights into how blood clots: Implication for the use of APTT and PT as coagulation screening tests and in monitoring anticoagulant therapy"; Semin. Thromb. Hemost. 1999; 25:407-418. These tests are further limited by the absence of active platelets.

In contrast, mechanical methods, such as the Thromboelastogram (TEG) and SonoClot, measure the contribution of all the components of hemostasis in whole blood. These methods have been widely studied and shown to offer valuable clinical and scientific insights, see Ganter et al., "Coagulation Monitoring: Current Techniques and Clinical Use of Viscoelastic Point-of-Care Coagulation Devices"; Anesth. Analg. 2008; 106:1366-1374. However, they utilize complex and expensive mechanical transducers, resulting in instruments that are difficult to operate. In addition, the large mechanical strains (in the range of 8% to 16%) applied to the blood samples have been shown to interfere with clot formation and limit sensitivity and speed of the measurements, see Evans et al., "Rheometry and associated techniques for blood coagulation studies"; Med. Eng. Phys. 2008; 30:671-679 and Burghardt et al., "Nonlinear viscoelasticity and thromboelastograph: Studies on bovine plasma clots"; Biorheology 1995; 32:621-630.

It would be desirable to provide systems and methods to make repeated viscoelastic measurements of a whole blood sample, wherein such systems and methods are not impeded by applications of large mechanical strains, but which apply much smaller forces to measure dynamic changes of viscoelastic properties observed during clot formation and clot dissolution to characterize hemostatic function.

The present invention meets all of the above needs and desires as well as providing additional advantages as set forth in the detailed description below.

SUMMARY OF THE INVENTION

In one aspect of the present invention, a method of evaluating a mechanical property of a material is provided, including: directing a series of acoustic pulses into the material to physically displace a portion of the material; measuring displacement of the portion of the material; adaptively adjusting the force when the displacement measured is not within a predetermined range of displacement values; and computing a mechanical property value resultant from the displacement of the material.

In at least one embodiment, the method further includes directing another series of acoustic pulses into the material, wherein the another series of acoustic pulses is the same as the series of pulses previously directed into the material when the displacement measured is within the predetermined range, and wherein the another series of acoustic pulses is modified from the series of pulses previously directed into the material when the displacement measured is not within the predetermined range, to apply the adjusted force; and repeating the measuring, adaptively adjusting and computing steps after the directing another series of acoustic pulses into the material.

In at least one embodiment, the mechanical property value is a value of a time-dependent mechanical property.

In at least one embodiment, the material comprises blood, the method further comprising computing a hemostatic characteristic curve from the mechanical property values.

In at least one embodiment, the hemostatic characteristic curve comprises stiffness values.

In at least one embodiment, the method further includes outputting at least one of: a measurement value resulting from the measuring displacement of the portion of the material; and the mechanical property value.

In at least one embodiment, the method further includes outputting at least one value of the curve as a function of time or a value derived from the at least one value of the curve as a function of time.

In at least one embodiment, the measuring includes estimating displacement of the portion of the material measured by sonorheometry, using echoes returned from the portion of the material.

In at least one embodiment, the method includes calculating strain of the portion of the material displaced from the estimated displacement calculated from the returning echoes, wherein the adaptively adjusting comprises increasing the force when strain calculated is less than or equal to a predetermined noise threshold strain value, and decreasing the force when the strain calculated is greater than a predetermined maximum strain threshold.

In at least one embodiment, the increasing of the force comprises increasing a pulse repetition frequency of the series of acoustic pulses directed into the material, and wherein the decreasing of the force comprises decreasing the pulse repetition frequency of the series of acoustic pulses directed into the material.

In at least one embodiment, the increasing of the force comprises increasing a pulse intensity integral of the series of acoustic pulses directed into the material, and the decreasing of the force comprises decreasing the pulse intensity integral of the series of acoustic pulses directed into the material.

In at least one embodiment, the method includes estimating changes in path length from a location where the series of pulses are directed to the portion of the material by measuring differences in arrival times of echoes of the pulses from the portion of the material.

In at least one embodiment, the computing comprises forming an ensemble of the measured differences in arrival times, thereby forming a time-displacement curve that describes the mechanical property of the material being analyzed.

In at least one embodiment, the method includes forming a plurality of the time-displacement curves by repeating direction of series of pulses over time, adjusted adaptively for force applied, and estimating the changes in path length iteratively for a plurality of times; extrapolating displacement values from each the time-displacement curve; and plotting at least one of a relative compliance curve and a relative stiffness curve, using the extrapolated displacement values, as a function of time.

In at least one embodiment, the material comprises whole blood.

In at least one embodiment, the material comprises plasma.

In at least one embodiment, the method includes outputting a time to clot value based on relative stiffness of the whole blood computed as a function of time.

In at least one embodiment, the method includes calculating a clot formation rate based on relative stiffness of the whole blood computed as a function of time.

In at least one embodiment, the method includes calculating a maximum stiffness of the material over time.

In at least one embodiment, the method includes calculating a time to lysis of a clot formed in the whole blood material, wherein the time to lysis is based on the relative stiffness of the whole blood computed as a function of time.

In another aspect of the present invention, a system for evaluating a mechanical property of a material is provided, including: a transducer; a transmitter driver configured to drive the transducer to direct a series of acoustic pulses into the material to physically displace a portion of the material; a receiver amplifier configured to receive and amplify signals transduced from echoes of the pulses received by the transducer; a processor, and memory containing stored programming, the stored programming configured to be run by the processor to: adaptively adjust force applied by the acoustic pulses as they are directed into the material, to maintain physical displacement of the portion of the material within a predetermined displacement range; and compute a hemostatic characteristic curve of the material as a function of time during which the pulses are directed into the material.

In at least one embodiment, the mechanical property of the material characterizes a hemostatic function of a sample.

In at least one embodiment, the material comprises whole blood, the system further comprises a container configured to hold the material, and the material has low acoustic attenuation and low acoustic impedance similar to that of blood In at least one embodiment, the system includes a heating element configured to control temperature of the material.

In at least one embodiment, the system includes a water bath configured to hold the material, the water-bath being temperature controlled by a heating element.

In at least one embodiment, the system includes programming configured to be run by the processor to output at least one hemostatic value as a function of time or a value derived from the at least one hemostatic value as a function of time.

In at least one embodiment, the at least one hemostatic value comprises a stiffness value.

In at least one embodiment, the stiffness value is a relative stiffness value.

In at least one embodiment, the stiffness value is an absolute stiffness value.

In at least one embodiment, the system includes programming configured to be run by the processor to estimate displacement of the portion of the material measured by sonorheometry, using times of transmission of the pulses from the transducer and times of receipt of echoes corresponding respectively to the pulses, as returned from the portion of the material.

In at least one embodiment, the system includes programming configured to be run by the processor to calculate strain of the portion of the material displaced from the estimated displacement calculated from the times of the transmitted pulses and returning echoes, wherein the adaptively adjusting comprises increasing the force when strain calculated is less than or equal to a predetermined noise threshold strain value, and decreasing the force when the strain calculated is greater than a predetermined maximum strain threshold.

In at least one embodiment, the system includes programming configured to be run by the processor to control the transmitter to increase or decrease the force by increasing or decreasing, respectively, a pulse repetition frequency of the series of acoustic pulses directed into the material from the transducer.

In at least one embodiment, the system includes programming configured to be run by the processor to increase or decrease the force by increasing or decreasing, respectively, a pulse intensity integral of the series of acoustic pulses directed into the material from the transducer.

In at least one embodiment, the system includes programming configured to be run by the processor to estimate changes in path length from a location where the series of pulses are directed to the portion of the material by measuring differences in arrival times of echoes of the pulses from the portion of the material, relative to times of departure of the pulses from the transducer, corresponding respectively to the echoes.

In at least one embodiment, the system includes programming configured to be run by the processor to form an ensemble of the measured differences in arrival times, thereby forming a time-displacement curve that describes viscoelastic properties of the material being analyzed.

In at least one embodiment, the system includes a display; and programming configured to be run by the processor to form a plurality of the time-displacement curves by repeating direction of series of pulses over time, adjusted adaptively for force applied, and estimating the changes in path length iteratively for a plurality of times; extrapolate displacement values form each the time-displacement curve; and plot at least one of a relative compliance curve and a relative stiffness curve on the display, using the extrapolated displacement values, as a function of time.

In at least one embodiment, the material comprises whole blood.

In at least one embodiment, the system includes programming configured to be run by the processor to output a time to clot value based on the relative stiffness of the whole blood computed as a function of time.

In at least one embodiment, the system includes programming configured to be run by the processor to calculate a clot formation rate based on the relative stiffness of the whole blood computed as a function of time.

In at least one embodiment, the system includes programming configured to be run by the processor to calculate a maximum stiffness of the material over time.

In at least one embodiment, the system includes programming configured to be run by the processor to calculate a time to lysis of a clot formed in the whole blood material, wherein the time to lysis is based on the relative stiffness of the whole blood computed as a function of time.

In another aspect of the present invention, a method of evaluating hemostatic function of a sample is provided, including: applying force to the sample sufficient to physically displace a portion of the sample; measuring displacement of the sample; adaptively adjusting the force when the displacement measured is not within a predetermined range of displacement values, wherein the force is increased or decreased depending upon whether the measured displacement is below or above the predetermined range, respectively; and computing a mechanical property value resultant from the displacement of the sample.

In at least one embodiment, the method includes repeating the applying force, wherein the adjusted force is applied; and computing the mechanical property value of the sample resultant displacement of the sample from application of the adjusted force.

In at least one embodiment, the method includes measuring displacement of the sample resultant from application of the adjusted force; adaptively adjusting the adjusted force when the displacement measured is not within the predetermined range of displacement values, wherein the force is increased or decreased depending upon whether the measured displacement is below or above the predetermined range, respectively; and iterating the repeating and computing steps.

In at least one embodiment, the mechanical property value is a value of a time-dependent mechanical property.

In at least one embodiment, the method includes repeating the applying force, whether or not the force has been adaptively adjusted; and computing a mechanical property value of the sample resultant from the repeating the applying force.

In at least one embodiment, the method includes iterating the repeating and the computing a mechanical property value of the sample resulting from the computing at least once.

In at least one embodiment, the mechanical property value is a value of a time-dependent mechanical property.

In at least one embodiment, the method includes computing a hemostatic characteristic curve from the mechanical property values.

In another aspect of the present invention, a system for evaluating hemostatic function of a sample is provided, including: a force applicator; a sensor configured to sense an amount of physical displacement or strain of a portion of the sample; a processor; and memory containing stored programming, the stored programming configured to be run by the processor to: adaptively adjust force applied by the force applicator pulses as the force is directed into the sample, to maintain physical displacement or strain of the portion of the sample within a predetermined displacement or strain range; and compute a mechanical property value resultant from the displacement of the sample.

In at least one embodiment, the mechanical property value is a value of a time-dependent mechanical property.

These and other features of the invention will become apparent to those persons skilled in the art upon reading the details of the methods and systems as more fully described below.

DETAILED DESCRIPTION OF THE INVENTION

Figure 1A:
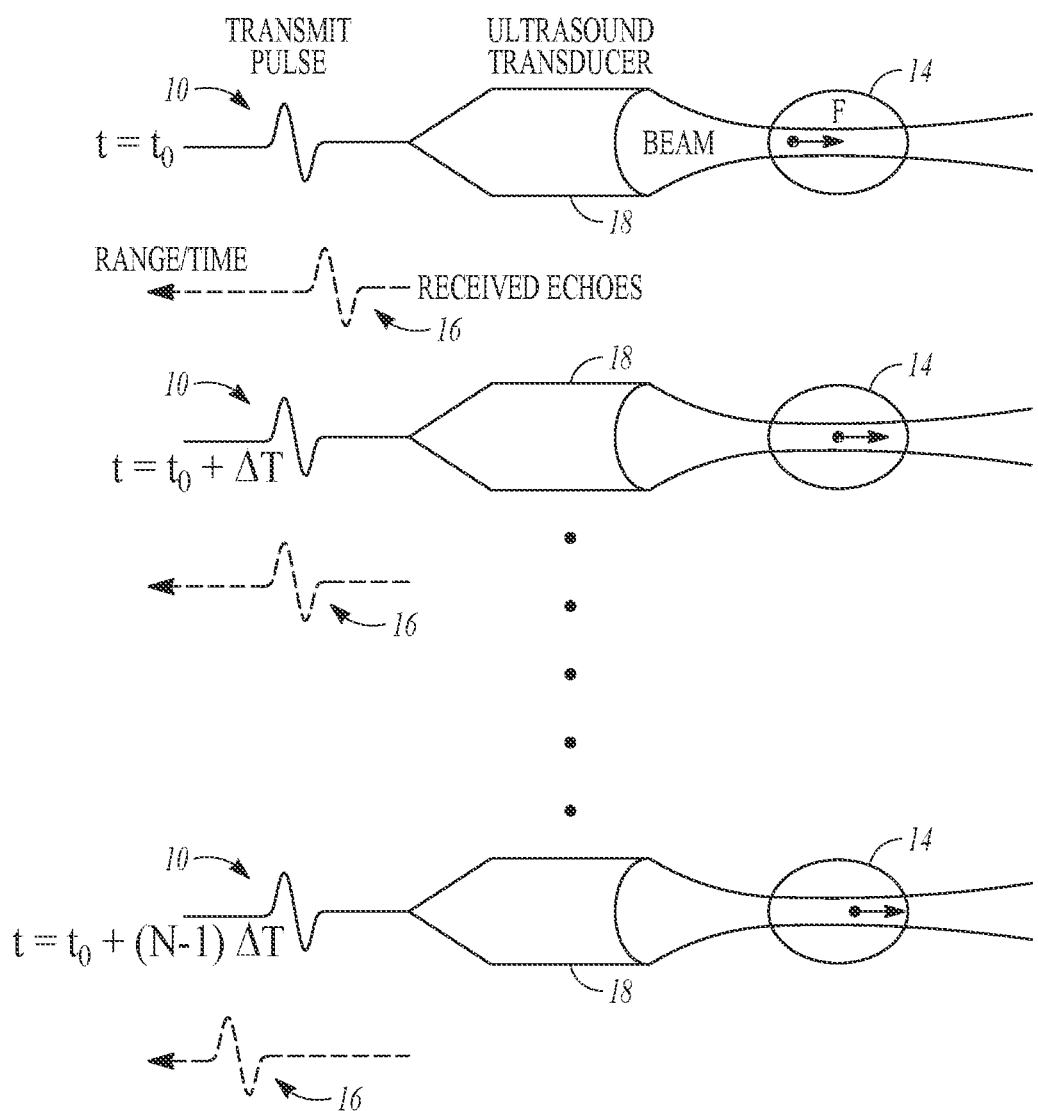
FIG. 1A is a schematic illustration showing application of acoustic pulses to a blood sample to perform sonorheometry according to an embodiment of the present invention.

Before the present systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and the include plural referents unless the context clearly dictates otherwise. Thus, for example, reference to "a curve" includes a plurality of such curves and reference to "the transducer" includes reference to one or more transducers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "pulse" as used herein, refers to a finite duration burst of acoustic energy. One or ordinary skill in the art would recognize that a pulse can also be defined as a wave of short temporal duration, relative to a time period over which an experiment or procedure is conducted.

An "echo" as used herein refers to acoustic energy reflected from an inhomogeneity.

"Acoustic radiation force" generally refers to a force generated by the transfer of momentum between an acoustic wave to a reflecting or absorbing target.

A "perfect absorber" as used herein, refers to a material that absorbs all the impinging acoustic energy.

"Attenuation", commonly represented mathematically as "$\alpha$" is defined as the loss of acoustic energy during propagation.

"Pulse intensity integral" or "PII" refers to the instantaneous intensity of a pulse integrated over the time where the acoustic pressure is nonzero. See also, Torr et al., "The Acoustic Radiation Force", Am. J. Phys. 1984; 52:402-408 ad Starritt et al., "Forces acting in the direction of propagation in pulsed ultrasound fields"; Phys. Med. Biol. 1991; 36:1465-1474, both of which are hereby incorporated herein, in their entireties, by reference thereto.

"Pulse repetition frequency" or "PRF" refers to the rate at which acoustic pulses are emitted.

Systems and Methods

While it is known that pathological alterations of the mechanical properties of blood clots are intimately related to thrombotic and hemorrhagic disease, it is essential to analyze every component of hemostasis and their interactions to fully characterize these properties. The balance between clotting factors, fibrin, platelets, and fibrinolytic proteins has great importance in determining the overall viscoelasticity of blood clots.

In one aspect of the present invention, sonorheometry is used to quantify the dynamic changes in mechanical properties of whole blood during the process of coagulation and clot dissolution, and thus provides information about the relative contribution of the coagulation factors, platelets, and fibrinolytic proteins to overall hemostatic function.

In one aspect, the present invention provides systems and methods to assess hemostasis function from a small sample of blood, using sonorheometry. In at least one embodiment, the present invention provide an in vitro, point-of-care (POC) blood test device that uses acoustic radiation force to quantify mechanical properties of the blood as it clots and that measures relative stiffness of the blood in real time. Sonorheometry uses the phenomenon of acoustic radiation force to measure the dynamic changes in blood viscoelasticity during clot formation and clot dissolution. Included below are descriptions of in vitro experiments using whole blood samples of 1 ml to demonstrate that sonorheometry is indicative of hemostatic functions that depend on plasma coagulation factors, platelets, and plasma fibrinolytic factors.

Sonorheometry measurements show titration effects to compounds known to alter the coagulation factors (GPRP peptide, 0 to 8 mM), platelets (abciximab, 0 to 12 ug/ml), and fibrinolytic factors (urokinase, 0 to 200 U). Repeated measurements of blood samples from the same subjects yielded reproducibility errors on the order of 5%, showing that sonorheometry accurately quantifies the functional role of the components of hemostasis in vitro.

The present systems and methods use an ultrasound-based technology, named sonorheometry, which uses the phenomenon of acoustic radiation force to make repeated viscoelastic measurements of a whole blood sample. The dynamic changes of viscoelastic properties observed during clot formation and clot dissolution are representative of hemostatic function. Thus the present invention is capable of using sonorheometry to measure the function of plasma coagulation factors (including fibrinogen), platelets, and fibrinolytic factors from a small sample of whole blood.

Acoustic radiation force can be described as the transfer of momentum between an acoustic wave (or pulse) and a reflection or absorbing target. As a result of the transferred momentum, the target experiences a small unidirectional force in the direction of the wave (or pulse) propagation. For a perfect absorber, this can be mathematically defined as follows:

$$|F| = \frac{2\alpha \langle I(t) \rangle}{c} = \frac{2\alpha PII}{c} PRF \quad (1)$$

where |F| is acoustic radiation force (in units of $m^{-1}$), $\alpha$ is the attenuation coefficient of the medium, c (in units of m/s) is the speed of sound in the medium, I(t) (in units of W/m2) is the instantaneous intensity of the beam (e.g., ultrasound beam), PII is pulse intensity integral, and PRF is pulse repetition frequency (typically measured in hertz), which characterizes the time interval between pulse or wave firings.

In order to exploit the acoustic radiation force phenomenon as a means to discern material properties of tissue, sonorheometry can be performed as a series of pulses transmitted so that the temporal characteristic of the acoustic radiation force approximates a step-function. In this stepwise radiation force that is applied, the resultant displacement profiles mimic responses observed in viscoelastic creep tests and can be described by viscoelastic models such as the Voigt or Kelvin models. Parameters such as steady-state displacement or time constants can be extracted which characterize material properties of the tissue that the acoustic force radiation is applied to. When the target tissue is whole blood, sonorheometry as described herein can be used to monitor coagulation and dissolution properties of the whole blood.

Sonorheometry is performed using acoustic radiation force as a means to generate small and localized displacements within a sample, e.g., a whole blood sample. Returned echoes are processed to measure the induced displacements and determine viscoelastic properties of the sample. In at least one embodiment, displacements are quantified using a principal component-based estimator technique, as described in Mauldin, Jr. et al., "Reduction of echo decorrelation via complex principal component filtering," *Ultrasound Med. Biol.*, vol. 35, no. 8, pp. 1325-1343, 2009 and in U.S. Pat. No. 12,467,216 filed May 15, 2009 and titled "Reduction of Echo Decorrelation in Ultrasonic Motion Estimation", both of which are hereby incorporated herein, in their entireties, by reference thereto.

In performing sonorheometry according to the present invention, for each measurement, a series of N ultrasound pulses 10 (where N=a positive integer) are fired toward a specified location within a blood sample 14 at time intervals ΔT, e.g., see FIG. 1A. Each pulse generates radiation force 12 as energy is absorbed and reflected during propagation. This radiation force 12 induces displacements within the blood sample 14 that depend upon local force application and mechanical properties of the blood. Each pulse 10 also returns an echo 16 as a portion of its energy is reflected from cell/plasma interfaces within the blood. Because the tissue (blood) moves slightly from one transmission to the next, the path length between the ultrasound transducer 18 and any given region within the target (blood) 14 changes with pulse number. This change in path length can be readily estimated from differences in the arrival times of echoes 16 from the same region, thereby accomplishing motion tracking of the sample. The series of N acoustic pulses are sent into the blood sample 14 at a specified pulse repetition frequency (PRF). These pulses 10 generate acoustic radiation force that induces a deformation field within the sample 14. The deformation field can be estimated from the time delays of the N returning echoes.

Figures 1B, 1C:
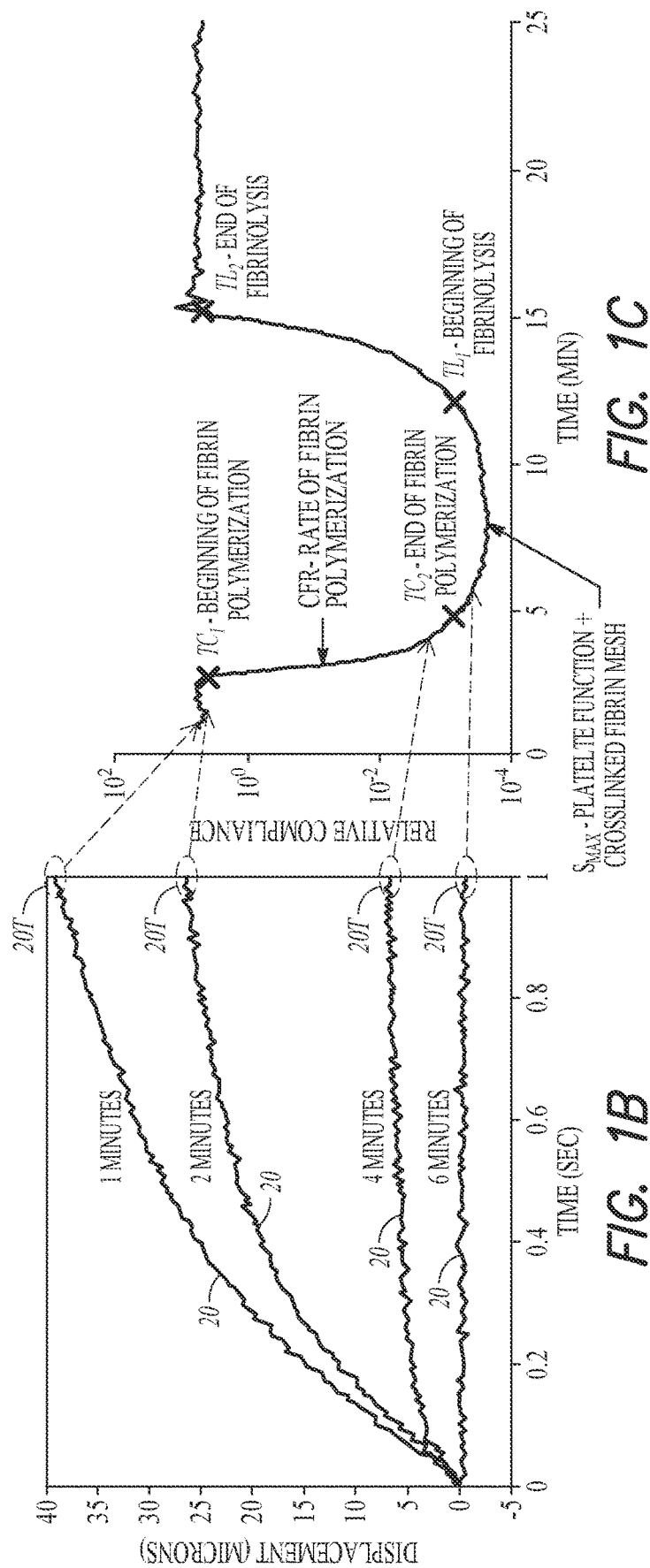
FIG. 1B illustrates examples of time-delay displacement curves formed as ensembles of the time delays according to an embodiment of the present invention.
FIG. 1C illustrates relative compliance curve, formed according to an embodiment of the present invention.

The ensemble of the time delays forms a time-displacement curve 20 that describes the viscoelastic properties of the sample being analyzed, see FIG. 1B. This process is then repeated M times (where M is a positive integer), with intervening relaxation periods, to provide data about the dynamics of clot formation and dissolution. As blood coagulates reduction in displacement is observed.

As the blood rapidly changes from viscous fluid to viscoelastic solid during coagulation and then back to viscous fluid after clot lysis, the applied acoustic radiation force is adaptively changed according to the present invention to induce displacements above a noise threshold, but below levels that could interfere with the physiological hemostatic process, such as by inducing mechanical disruption of tissues, etc. The noise threshold is determined empirically so as to provide an adequate signal-to-noise ratio without inducing physiologically disruptive strains. The magnitude of the acoustic radiation force is adjusted to follow changes that occur in mechanical properties of the blood sample during the changes from viscous fluid to viscoelastic fluid back to viscous fluid, while keeping the strain below 3%, and thus within the linear range where elasticity is independent of strain amplitude, see Burghardt et al., "Nonlinear viscoelasticity and thromboelastograph.1. Studies on bovine plasma clots"; Biorheology 1995; 32:621-630, which is hereby incorporated herein, in its entirety, by reference thereto. According to equation (1), in order to alter the acoustic radiation force, which is a function of the pulse intensity integral (PII) and pulse repetition frequency (PRF), the PRF can be changed by firing pulses within shorter or longer intervals. Alternatively, or additionally, the PII can be changed by changing the pulse length and/or pulse amplitude and/or pulse frequency, for example.

The attenuation α and speed of sound c cannot be changed, as they are constants relative to the material that the force is being applied to and through. However, in the case of hemostasis, α and c do change somewhat during coagulation and fibrinolysis, as the material itself to and through which the force is applied changes. The present invention measures these changes by measuring transit time and attenuation through the sample by placing a second receiving transducer opposite to the transmitter transducer. Alternatively, a known reflector can be placed at some known distance from the transmitter transducer and the arrival time and magnitude of echoes from the reflector can be used to quantify speed of sound and attenuation, respectively. By combining these measurements with the known PII and PRF (or I(t)), the acoustic radiation force can be calculated and absolute stiffness and compliance values (as opposed to merely measuring or calculating relative changes in stiffness and compliance) can be calculated for the material that the force is applied to and through.

Specifically, the steady state displacement induced during the $(m-1)^{st}$ acquisition is used to determine whether the force should be increased or decreased for the $m^{th}$ acquisition, based on predetermined threshold values (with in =1, . . . , M). Alternatively, other parameters can be monitored to indicate when to adapt the acoustic radiation force applied. For example, the maximum displacement induced during the acquisition interval (which may be less than the steady state displacement) may be used to guide force application. Additionally, the time constant of the viscoelastic response of the material may be used to guide the applied force. This adaptive process permits characterization of over five orders of magnitude in mechanical properties without generating high strain within the blood sample that could alter the underlying physiological processes. The values of the M steady-state displacements are combined to form a relative compliance curve 30 that is representative of the hemostatic process, e.g., see FIG. 1C. The compliance parameter is referred to as "relative" since the absolute magnitude of the radiation force is unknown due to its dependency on blood acoustic properties, which change throughout coagulation, e.g., see Shung et al., "Ultrasonic Characterization of Blood During Coagulation"; J. Clin. Ultrasound 1984; 12:147-153, which is hereby incorporated herein, in its entirety, by reference thereto. Alternatively, as noted above, the changes in acoustic properties (i.e., changes in acoustic attenuation α and speed of sound c) can be measured so that acoustic radiation force can be calculated and absolute stiffness and compliance values can be calculated according to the present invention.

In FIG. 1C, the relative compliance curve 30 shows characteristic features labeled $TC_1$, $TC_2$, CFR, S, $TL_1$, and $TL_2$. The hemostasis parameters indicated in FIG. 1C are calculated by first fitting the sonorheometry relative stiffness data to a modified sigmoidal function such as, for example, the following model (although other models may be alternatively used to accomplish these calculations (such as a combination of linear trends or a combination of skewed error functions):

$$f(t) = \alpha \frac{t^\beta}{1 + e^{-\left(\frac{t-\gamma}{\delta}\right)\sigma}} + \varepsilon \quad (2)$$

where t is experimental time (in seconds) and α, β, γ, δ and ε are parameters determined to best fit the model curve to the data.

The parameter $TC_1$ corresponds to the rapid decrease in relative compliance observed in FIG. 1C. $TC_1$ is referred to as "time to clot" and the time value indicative of the beginning of fibrin polymerization. Similarly, the parameter $TC_2$ represents the ending of fibrin polymerization. The parameter CFR (clot formation rate) is the slope of the plot 30 during fibrin polymerization, which extends generally between $TC_1$ and $TC_2$. The slope can be determined as an average slope, a peak slope, or some other measure of the slope. The slope is indicative of the rate of fibrin polymerization. A definition of CFR is utilized as the maximum value of the derivative of equation (2). Additionally or alternatively to calculation of CFR as described, an angle θ can be defined as the slope of the line between $TC_1$ and $TC_2$. The feature $S_{MAX}$ (maximum stiffness) is the minimum achieved relative compliance (minimum value of plot 30), corresponding to the maximum stiffness of the clot. The maximum stiffness $S_{MAX}$ depends upon platelet function and the stiffness of the fibrin network. The times $TL_1$ and $TL_2$ can be defined to represent the initial and final phases of the fibrinolytic process and the consequent dissolution of the fibrin network (time to lysis) $TL_1$, indicating the "lysis initiation time", and $TL_2$, indicating the "end of lysis time", can be calculated by defining a new sigmoidal curve similar to that defined by equation (2), calculating the curve derivative, and estimating the times corresponding, for example, to twenty percent of the minimum of the derivative. Thus steady-state displacements are combined to form graphs of relative compliance, which characterize the overall hemostatic process.

Assuming a linear viscoelastic response, which holds for blood at strains less than about 3% or less than approximately 2-3%, the elastic modulus of blood is linearly related to the quotient of the applied force and the steady-state displacement. Thus an estimate of the relative stiffness of the blood can be calculated as follows:

$$S = \Phi \frac{PRF}{u_{ss}} \quad (3)$$

where $\mu_{ss}$ is the estimated steady state displacement 20 T and $\Phi$ is a constant that incorporates the geometry of the sample (including boundary conditions), attenuation, speed of sound (in the medium through which the wave or pulse is propagating), and pulse intensity. Measurements of displacement are typically, but need not be, taken at regular predefined intervals of time and compiled to form a characteristic sonorheometry curve 20 as illustrated in FIG. 1B.

Due to the large range of elasticity values in whole blood during hemostasis, the use of a fixed force to measure all stiffness levels is done at the cost of applying high strains. Alternatively, if strains are maintained at less than three percent while a fixed force is applied, the dynamic range of stiffness measurable is limited to as little as two orders of magnitude and therefore the ability to measure physiologic change is greatly reduced. Since it has been demonstrated that high strains (i.e., strains greater than three percent) dramatically and negatively impact hemostasis, including a prolonged clotting time and decreased clot stiffness, the present invention performs measurements at low strain to avoid these dramatic, negative effects.

In order to perform measurements at low strain, the present invention uses adaptive force sonorheometry to achieve both low levels of strain and a large dynamic range of measurement. As illustrated by equation (1), the magnitude of radiation force can be controlled by changing the PRF. Another method of altering the magnitude of the radiation force is by altering the pulse duration of the radiation pulses applied.

Figure 2:
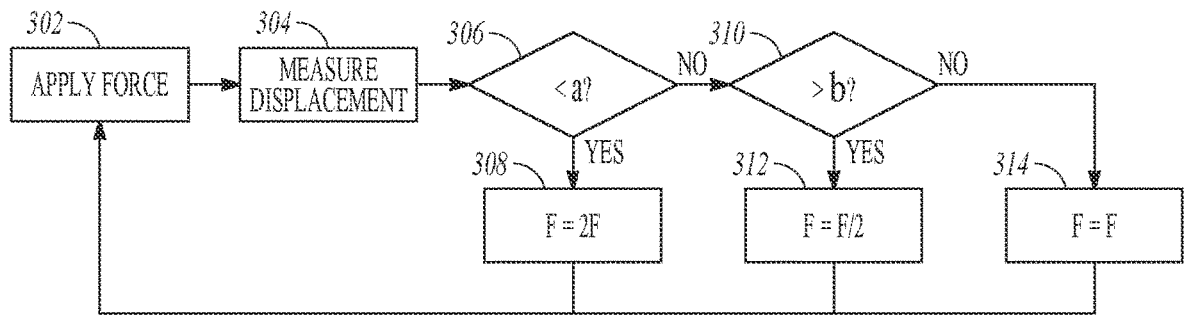
FIG. 2 is a flow chart illustrating an example of the principle of applying adaptive force to a sample for high dynamic range measurement performed at low strain levels according to an embodiment of the present invention.

FIG. 2 is a flow chart illustrating an example of the principle of applying adaptive force to a sample for high dynamic range measurement performed at low strain levels according to an embodiment of the present invention. In this embodiment, a minimum displacement threshold level "a" and a maximum displacement threshold level "b" are preset prior to application of force. At event 302, force F is applied to the target being measured according to an embodiment of the present invention. At event 304 a displacement of the target that resulted from application of the force F to the target in event 302 is measured. At event 306, the measured displacement is compared to the minimum displacement threshold level "a". If the measured displacement is less than "a", then the force F is increased at event 308 (e.g., doubled, in the embodiment shown in FIG. 2) and this greater force is then applied at event 302 to take the next measurement at event 304. If, on the other hand, the measured displacement not less than "a", then a comparison is made at event 310 as to whether the measured displacement is greater than maximum displacement threshold level "b". If the measured displacement is greater than "b", then the force is reduced at event 312 (e.g., halved, in the embodiment shown in FIG. 2) and this lesser force is then applied at event 302 to take the next measurement at event 304. If, on the other hand, the measured displacement not greater than "b", then the force is maintained at its current level at event 314 and the same force is applied at event 302 for taking the next measurement. In the present invention, an increase of the force F is accomplished by increasing the PRF. Conversely, a decrease of the force F is achieved by decreasing the PRF. Using the principle described with regard to FIG. 2, the present invention can carry out sonorheometry at low strains with a dynamic range of stiffness measurements of approximately five orders of magnitude. Of course, the present invention is not limited to increasing by doubling or decreasing by half, as any arbitrary multipliers (greater than one for increasing, and less than one but greater than zero for decreasing) can be implemented to carry out the described principle. Likewise, as noted above, increasing and decreasing functions need not be limited to changing the PRF, as these can alternatively be carried out by changing the PII or by changing both PRF and PII.

Figure 3:
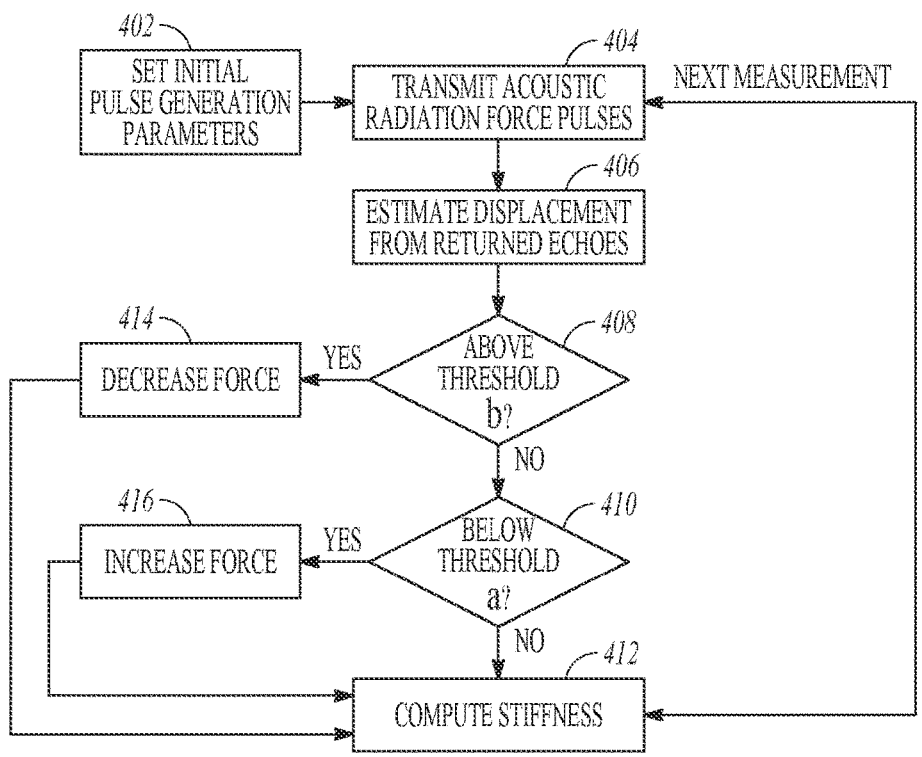
FIG. 3 is a flow chart illustrating use of adaptive radiation force sonorheometry to adaptively adjust the applied radiation force in order to maintain low strains and improve dynamic ranges of stiffness measurement according to an embodiment of the present invention.

FIG. 3 is a flow chart illustrating use of adaptive radiation force sonorheometry to adaptively adjust the applied radiation force in order to maintain low strains and improve dynamic ranges of stiffness measurement according to an embodiment of the present invention. At event 402, initial parameters are set for PRF and PII, thus defining the initial pulse generation parameters. Typically the initial PRF is set at a value with the rang of from about 4 Hz to about 12 kHz, or less than or equal to 100 Hz, although the present invention is not limited to these settings. Pulses with as little as one cycle up to pulses with as many as sixteen cycles have been used. Amplitude may be varied such as increasing (up to doubling, or more) or decreasing (down to halving, or less). In cases where an emission transducer of relatively low efficiency is used, PRF and PII may be set relatively higher. For applications to plasma, which has a lower viscosity than whole blood, relatively lower PII and PRF may be set.

At event 404, acoustic radiation force pulses are transmitted to the target according to the PRF and PII that were initially set in event 402. At event 406 a displacement of the target is estimated or measured by sonorheometry, using echoes returned from the target. At event 408, the estimated displacement value is compared with the maximum displacement threshold value "b". If the estimated displacement value is greater than "b", then the force to be applied to the target in the next iteration is set to be decreased by decreasing the PRF and/or decreasing the PII at event 414 and a relative stiffness value (or absolute stiffness value in embodiments where the constants α and c are measured) is computed at event 412, using the estimated displacement value. Next, event 404 is carried out again by transmitting decreased force generated using the parameters from event 414.

If, on the other hand, the estimated or measured displacement value is not greater than "b" at event 408, then at event 410 the estimated displacement value is compared with the minimum displacement threshold value "a". If the estimated displacement value is less than "a", then the force to be applied to the target in the next iteration is set to be increased by increasing the PRF and/or increasing the PII at event 416 and a relative stiffness value (or absolute stiffness value in embodiments where the constants α and c are measured) is computed at event 412, using the estimated displacement value. Next, event 404 is carried out again by transmitting increased force generated using the parameters from event 414. Iterations can be carried out until all physiological observations that the observer is interested in have been made, e.g., until an experiment is ended, until a patient is released to another care center, until a clot completely dissolves, etc.

Figure 4:
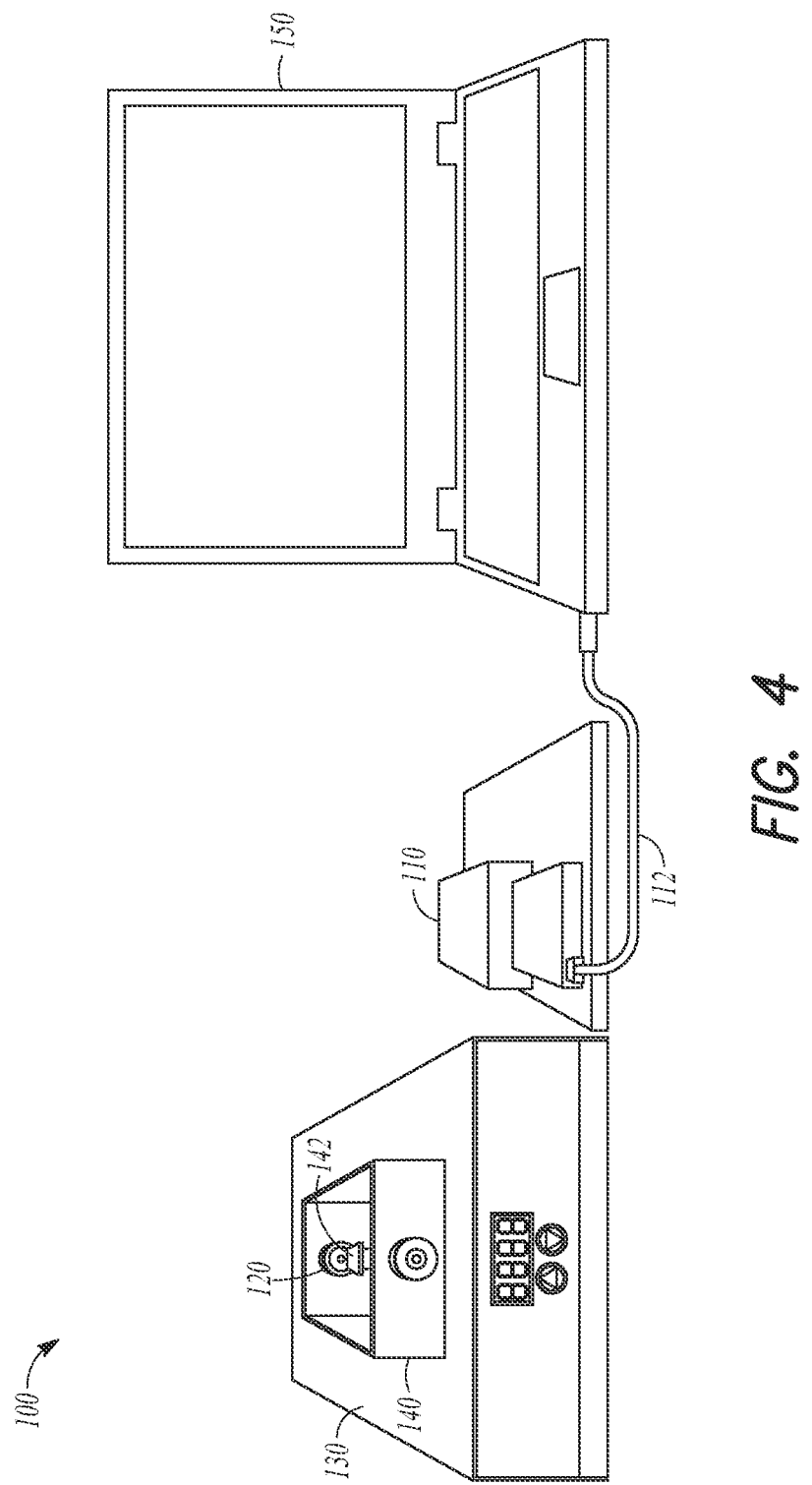
FIG. 4 shows a system for performing sonorheometry according to an embodiment of the present invention.

Turning now to FIG. 4 a system 100 for performing sonorheometry is provided according to an embodiment of the present invention. System 100 includes a custom printed circuit board (PCB) 110 controlled by computer 150, as shown. It is noted that although an external, laptop computer 150 is shown in FIG. 4, the present invention is not limited to this arrangement, as a desktop computer or other type of computer capable of carrying out the necessary calculations at sufficient speeds for carrying out the present methods may be substituted. Likewise, custom PCB 110 does not necessarily have to be external to computer 150, but could, alternatively, be incorporated with computer 150 into a single instrument. In the embodiment shown, PCB 110 is connected to laptop computer 150 via a USB 2.0 connection 112. Of course, other high speed connection hardware may be substituted to perform the same functions.

In FIG. 4, PCB 110 has circuitry for two transmit and four receive ultrasound channels. However, the present invention is not limited to these numbers of transmit and receive channels, as more or fewer may be provided. In another embodiment (not shown) tow transmitters and two receivers are used with eight test wells and a multiplexer to selected between the test wells.

For the experiments described below, the same transducer was used to transmit pulses 10 to and receive echoes 16 from the blood samples 14. An off the shelf, readily available dry block heater 130 (Digital One Dry Block Heater, available form Fisher Scientific) and a custom made water-filled aluminum chamber 140 (although it could be made of virtually any other material that will hold water) were used to control the temperature of the sample 14 being analyzed, while providing ultrasound coupling between the sample 14 and transducer 120. Although water was used, other media could be substituted, such as any acoustically transparent material including fluids or solids The received echoes are converted by the transducer 120 to electrical signal data and the electrical signal data are filtered and digitized within the PCB 110 and sent to the computer 150 for further analysis.

In one embodiment, system 100 supports two transmit and four receive ultrasound channels. The transmitter (transmit channel) utilizes five-voltage levels and is composed of adjustable high voltage sources and high-speed transmitter drivers. High voltage supplies that were used were the Q-05 from Pico Electronics. Transmitters were built using SuperTex MD1711 chips to drive SuperTex TC6320 MOSFETS. Received echoes 16 are amplified using a variable gain amplifier, band-pass filtered, and then digitized at 65 MHz with 12-bit precision Alternatively, other sampling frequencies can be used so long as they fulfill the Nyquist sampling criteria. For 10 MHz ultrasound the sampling range must be at least 20 MHz, but practically, at least 30 MHz for reasonable bandwidths. There is not a maximum sampling frequency, but there is little to be gained by going much over a few hundred MHz.

The digitized data were then transferred to computer 150 for data analysis. The transducer 120 used in the experiments was a 10 MHz piston transducer with a 1 cm aperture, a 4 cm fixed focus, and roughly 50% fractional bandwidth (Olympus NDT Inc., Waltham, Mass.), although other transducers may be substituted, as the present invention is not limited to this particular species of transducer. Alternative types of transducers that can be used include, but are not limited to, piezoelectric, optoacoustic, thermoacoustic, and micromachined transducers that may be used to generate acoustic pulses and receive returned echoes.

Acoustic radiation force is induced by applying ultrasound pulses 10 (e.g., each 16 cycles long (although other cycle lengths could be used, as noted above; additionally, pulse length with a series may vary) at a PRF that is adaptively varied from 25 Hz to 12.8 KHz. Alternatively, variation of PRF may go as low as about 2 Hz and as high as about 16 kHz, or higher.

Blood samples 14 may be contained in cuvettes 142, such as cuvettes made from polystyrene or other material having low acoustic attenuation and acoustic impedance similar to that of the sample that it contains. In at least one embodiment, blood samples 14 were contained in off the shelf polystyrene cuvettes 142 (Fisher Scientific, Pittsburgh, Pa.) placed in the water filled chamber 140. The cuvettes 142 have low acoustic attenuation and acoustic impedance similar to that of blood; thereby allowing delivery of sufficient ultrasound pulses within the blood 14 to perform measurements. Sonorheometry measurements can be performed at regular intervals during coagulation and clot fibrinolysis. In at least one embodiment, sonorheometry measurements are made every six seconds during coagulation and clot fibrinolysis. However, the present invention is not limited to measurements every six seconds, as the time period may be greater than or less than six seconds. It is even possible to vary the lengths of time delay durations, although this is more complicated and would require more processing time, so is less practical.

The heating element 130 and water bath 140 are used to hold the samples 14 at a predetermined temperature, e.g., at body temperature for blood samples (typically about 37° C.; however, for a hypothermic patient, temperature may be as low as about 18° C. or somewhere between 18° C. and 37° C., and it may be advantageous to warm such a sample up to about 42° C.) while providing a propagation medium (water, in the system described here, or other acoustically transparent medium) for the ultrasound beam (pulses 10 and echoes 16. The system described in this embodiment is designed to hold the temperature of the sample at about 37° C.±0.5° C.

Figure 5:
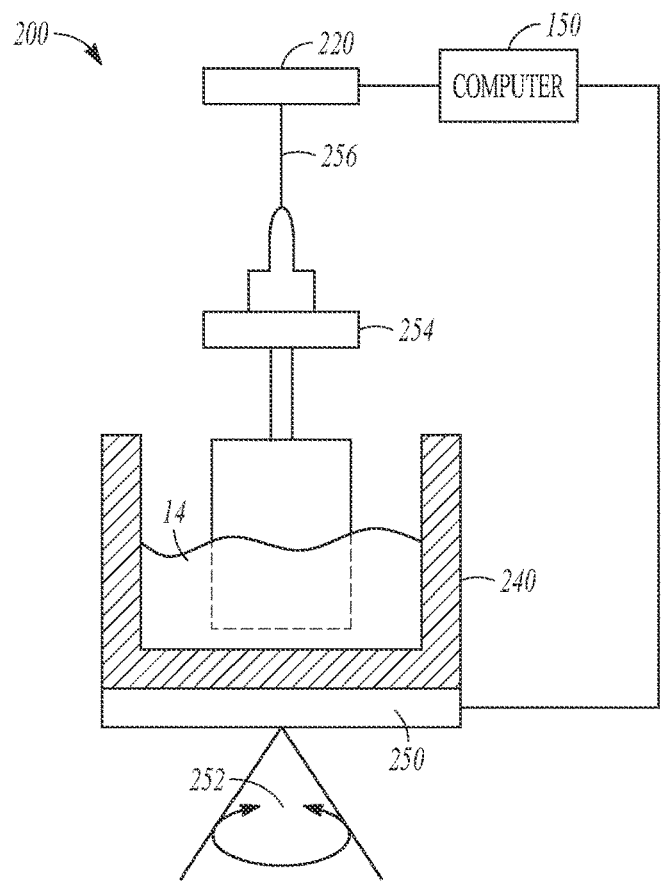
FIG. 5 schematically illustrates a system configured to mechanically apply force to deform a material so as to evaluate a mechanical property thereof, according to an embodiment of the present invention.

FIG. 5 schematically illustrates a system 200 configured to mechanically apply force to deform a material 14 so as to evaluate a mechanical property thereof (e.g., a hemostatic function of a blood sample 14, or other mechanical property of a blood sample or other material) and to adaptively apply force, as in other embodiments described herein. In this embodiment, adaptive force techniques are applied similar to those described in other embodiments, even though the mechanism for the generation/application of force is different.

Stationary container 240 holds the sample 14 (e.g., whole blood) to be analyzed. The container 240 is coupled to a drive mechanism 250 that causes the container 240 to oscillate through an angle 252. A pin 254 is suspended in the sample 14 by a torsion wire 256 and the pin 254 is monitored for motion. The torque of the rotating container 240 is transmitted to the immersed pin 254. In the case of a blood sample, the magnitude of the pin motion 254 increases as the clotting process progresses and viscosity increases. The rotational movement of the pin 254 is converted by transducer 220 to an electrical signal that is monitored by computer 150. Further mechanical operation of a system of this type can be found, for example in U.S. Pat. Nos. 7,732,213 and 6,225,126, both of which are hereby incorporated herein, in their entireties, by reference thereto.

As noted, as the blood transitions from a fluid to a solid clot, the mechanical resistance between the pin 254 and container 240 increases. This causes the pin 254 to be dragged through the rotational angle 252 as the clot strengthens. The torsion measured by the pin 254 (as transferred to the transducer 220 and converted to an electrical signal that is monitored by computer 150) is indicative of the mechanical properties of the sample 14 during the process of coagulation and fibrinolysis.

This type of system 200 has been reported to generate large mechanical strains as noted in the background section discussion of TEG above. These strains have been measured to be on the order of about 8% to about 16%. The present invention assesses the mechanical properties of the material 14, such as blood with low strain, according to the adaptive force techniques described herein. For example, by monitoring the torque n pin 254 via wire 256, transducer 220 and computer 150, computer 150 provides feedback to drive mechanism 250 to vary the angle 252 so as to maintain the strain within a predetermined range, such as below about 3%, but large enough to provide useful measurements of stiffness. Thus, for whole blood, at the beginning of processing, when the blood is still fluid, a relative small angle of rotation 252 is executed. As the blood coagulates and stiffness increases, computer 150 control drive mechanism 250 to apply increasingly larger angles of rotation 252. During clot dissolution, the angle 252 is reduced progressively.

Figure 6:
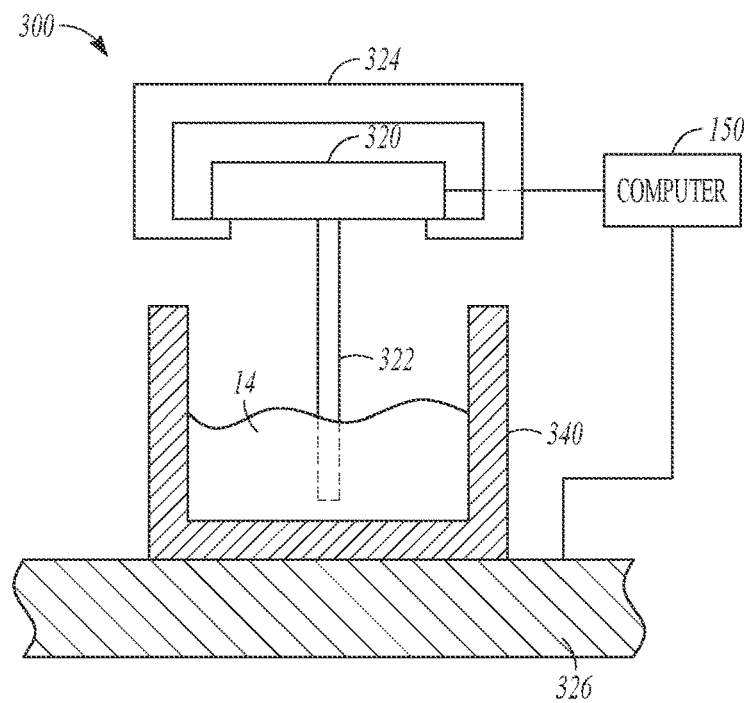
FIG. 6 schematically illustrates a system configured to mechanically apply force to deform a material so as to evaluate a mechanical property thereof, according to another embodiment of the present invention.

FIG. 6 schematically illustrates a system 300 configured to mechanically apply force to deform a material 14 so as to evaluate a mechanical property thereof (e.g., a hemostatic function of a blood sample 14, or other mechanical property of a blood sample or other material) and to adaptively apply force in performance of the evaluation, as in other embodiments described herein. System 300 is similar to the Sonoclot Analyzer, manufactured by Sienco, Inc. of Morrison Colo., and other types of systems like the Sonoclot, but is modified so as to adaptively apply force in a manner described herein. Further details about a Sonoclot type analyzer can be found, for example, in U.S. Pat. Nos. 5,138,872; 5,895,842; 6,192,744 and 6,632,678, each of which is hereby incorporate herein, in its entirety, by reference thereto.

System 300 includes a transducer 320 that is mechanically excited by a transducer drive voltage signal, which may be provided by and include in computer system 150, for example Probe 322 is attached to transducer 320 and is driven mechanically to oscillate at a resonant frequency of a sensor used to detect viscoelastic properties of a sample 14 that is contained in cuvette 340. The transducer and thus also the probe are mouthed to a head that is vertically movable so as to insert or withdraw the probe 322 from the sample 14. Optionally, a heating platen 326 may be provided in contact with cuvette 340, such that the temperature of the sample 14 in cuvette 340 can be monitored by a sensor (not shown) and computer 150 can be connected in a feedback loop to control heating platen 326 to maintain the temperature of the sample 14 within a desired range.

To operate the system 300, sample 14 is added to the cuvette 340 while the head 324 is in the raised position (not shown), so that probe 322 does not make contact with the sample. When platen 326 is supplied, sample 14 is next heated to the desired temperature. Once the desired temperature is achieved, a mixing motor (not shown) is activated to magnetically drive a magnetic mixing bar (not shown) in cuvette 340 to mix the sample. After a predetermined period of time (e.g., 10 seconds) stirring is halted and head assembly 324 is lowered so that probe is positioned in the sample 14, as shown in FIG. 6. The oscillation of probe 322 is resisted by the sample 14 and therefore the transducer 320 generates a signal that is responsive to and characteristic of viscous and elastic characteristics of the sample.

Because this type of system 300 can generate large mechanical strains via the oscillating probe 322, the present invention assesses the mechanical properties of the material 14, such as blood with low strain, according to the adaptive force techniques described herein. For example, by monitoring the probe 322 via transducer 320 and computer 150, computer 150 can provide feedback to the driver for driving the oscillation of the probe 322, to keep the measured strain within a predetermined range, such as below about 3%, but large enough to provide useful measurements of stiffness. Thus, for whole blood, at the beginning of processing, when the blood is still fluid, a relatively small angle of rotation is executed. As the blood coagulates and stiffness increases, computer 150 controls the oscillation of probe 322 via transducer 320 to apply increasingly larger angles of rotation. During clot dissolution, the angle of rotation is reduced progressively.

Figure 7:
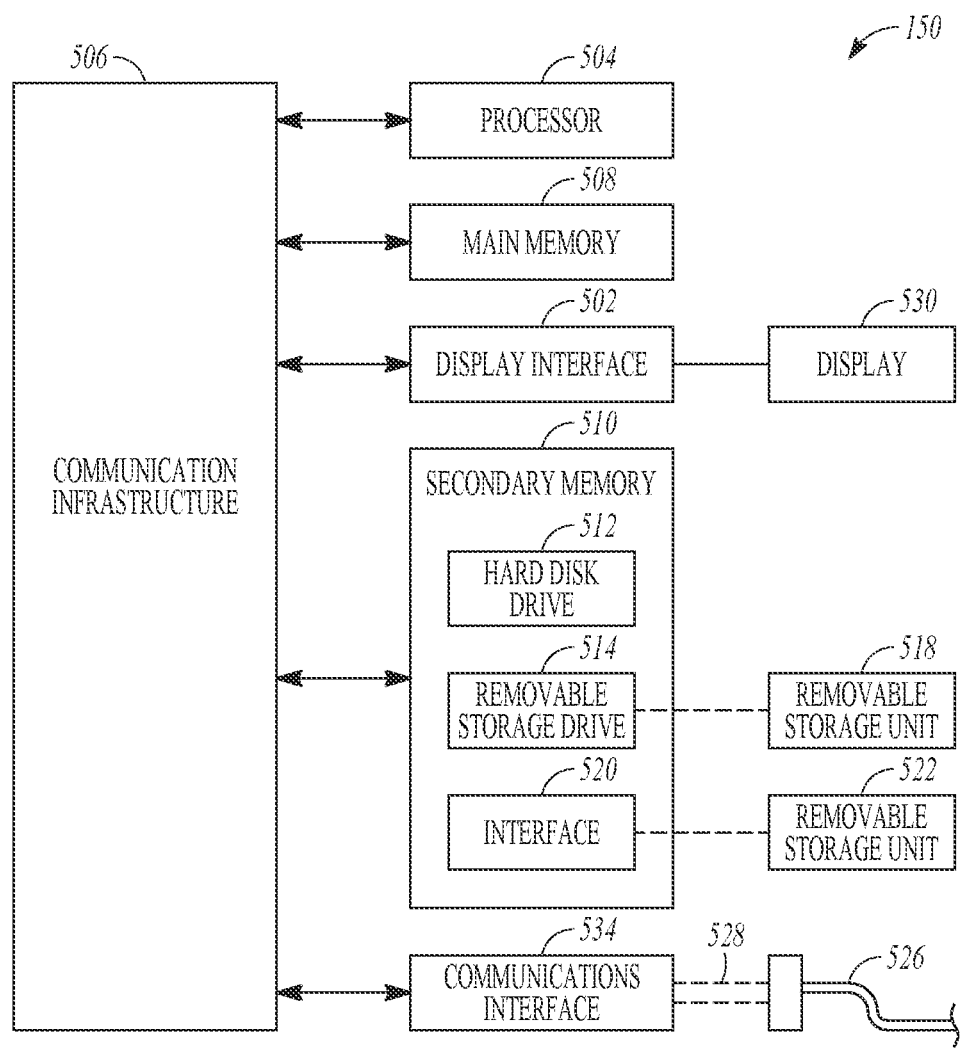
FIG. 7 is a schematic block diagram for a computer system for implementation of an exemplary embodiment or portion of an embodiment of the present invention.

FIG. 7 is a schematic block diagram for a computer system 150 for implementation of an exemplary embodiment or portion of an embodiment of the present invention. For example, a method or system of an embodiment of the present invention may be implemented using hardware, software or a combination thereof and may be implemented in one or more computer systems or other processing systems, such as personal digital assistants (PDAs) equipped with adequate memory and processing capabilities. In an exemplary embodiment, the invention was implemented in software running on a general purpose computer 150, such as laptop 150 illustrated in FIG. 4. In this and other embodiments, the computer system 150 may include one or more processors, such as processor 504. Processor 504 is connected to a communication infrastructure 506 (e.g., a communications bus, cross-over bar, or network). The computer system 150 may include a display interface 502 that forwards graphics, text, and/or other data from the communication infrastructure 506 (or from a frame buffer not shown) for display on the display unit 530. Display unit 530 may be digital and/or analog.

The computer system 150 may also include a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, a flash memory, etc. The removable storage drive 514 reads from and/or writes to a removable storage unit 518 in a well known manner. Removable storage unit 518 represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other means for allowing computer programs or other instructions to be loaded into computer system 150. Such means may include, for example, a removable storage unit 522 and an interface 520. Examples of such removable storage units/interfaces include a program cartridge and cartridge interface (such as that found in video game devices), a removable memory chip (such as a ROM, PROM, EPROM or EEPROM) and associated socket, and other removable storage units 522 and interfaces 520 which allow software and data to be transferred from the removable storage unit 522 to computer system 150.

The computer system 150 may also include a communications interface 534. Communications interface 534 allows software and data to be transferred between computer system 150 and external devices. Examples of communications interface 534 may include a modem, a network interface (such as an Ethernet card), a communications port (e.g., serial or parallel, etc.), USB port, a PCMCIA slot and card, a modem, etc. Software and data transferred via communications interface 534 are in the form of signals 528 which may be electronic, electromagnetic, optical or other signals capable of being received by communications interface 534. Signals 528 are provided to communications interface 534 via a communications path (i.e., channel) 528. Channel 528 (or any other communication means or channel disclosed herein) carries signals 528 and may be implemented using wire or cable, fiber optics, blue tooth, a phone line, a cellular phone link, an RF link, an infrared link, wireless link or connection and other communications channels.

In this document, the terms "computer program medium" and "computer usable medium" and "computer program product" are used to generally refer to media or medium such as various software, firmware, disks, drives, removable storage drive 514, a hard disk installed in hard disk drive 512, and signals 528. These computer program products ("computer program medium" and "computer usable medium") are means for providing software to computer system 150. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 508 and/or secondary memory 510. Computer programs may also be received via communications interface 534. Such computer programs, when executed, enable computer system 150 to perform the features of the present invention as discussed herein. In particular, the computer programs, when executed, enable processor 504 to perform functions of the present invention. Accordingly, such computer programs represent controllers of computer system 150.

In an embodiment where the invention is implemented using software, the software may be stored in a computer program product and loaded into computer system 150 using removable storage drive 514, hard drive 512 or communications interface 534. The control logic (software or computer program logic), when executed by the processor 504, causes the processor 504 to perform functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an exemplary software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Blood samples were obtained from a peripheral vein of the arm of a patient into six 1.8 ml Vacutainers™ (Becton Dickinson, Franklin Lakes, N.J.) containing 3.2% (0.105M) sodium citrate to prevent coagulation within the tubes. The first tube was discarded, while the remaining tubes were placed on a rocker table and analyzed sequentially starting thirty minutes after the draw. For all the experiments described here, samples were obtained from a total of eight volunteers (four male and four female) with age range of twenty-three to thirty years (mean and standard deviation of 25.75±3.3 years) and with no history of thrombotic or hemorrhagic disorders. Ultrasound pulses having 10 Mhz center frequency were applied, PRF was adaptively adjusted with the range of about 25 Hz to about 12.8 kHz. Automated measurements having a one second acquisition time were performed every six seconds.

In a typical experiment, 1 ml of citrated blood was pipetted into a 4 ml clear polystyrene cuvette 142 along with 0.5 mg of kaolin activator to start coagulation through activation of the intrinsic pathway and 62 µl of 0.2M $CaCl_2$ to reverse the anticoagulant effect of the sodium citrate. Other reagents were also added as required by the specific study performed. Phosphate Buffer Saline (PBS) solution was added to maintain identical blood dilution. Sonorheometry data acquisition was initiated one minute after all the reagents were pipetted into the sample, and measurements were performed every six seconds.

Gly-Pro-Arg-Pro (GPRP) was obtained from Calbiochem (EMD Chemicals Inc., Gibbstown, N.J.) with 99.1% purity as determined by HPLC. GPRP was dissolved in PBS into 100 mM stock. Kaolin was obtained in powder form (Sigma Aldrich, St. Louis, Mo.) and suspended in sterile sodium chloride solution (Becton Dickinson, Franklin Lakes, N.J.). Monoclonal antibody abciximab (ReoPro®, Eli Lilly and Company, Indianapolis, Ind.) was obtained in a concentration of 2 mg/ml. The original solution was diluted by a factor of five by adding 200 µL of PBS into 50 µl of the original ReoPro solution. The serine protease abbokinase (urokinase-type Plasminogen Activator, or uPA, Hyphen Biomed, Neuville-sur-Oise, France) was obtained in a concentration of 1 unit/µl.

The raw ultrasound data were transferred from the custom PCB 110 to the laptop computer 150 through USB interface 112 and analyzed in MATLAB (MathWorks Inc., Natick, Mass.). The data were first processed using a principal component filter to further remove noise and clutter due to reverberation and internal reflections within the cuvette 142, as described by Mauldin Jr. F W, Viola F, Walker W F. Reduction of Echo Decorrelation via Complex Principal Component Filtering. Ultrasound Med Biol 2009; 35:1325-1343, incorporated by reference above. Pulse-to-pulse time delays were estimated using a spline-based estimator as described in Viola F, Walker W F. A Spline Based Algorithm for Continuous Time Delay Estimation Using Sampled Data. IEEE Trans Ultrason Ferroelect Freq Cont 2005; 52:80-93, which is hereby incorporated herein, in its entirety, by reference thereto, and assembled to generate time-displacement curves 20, similar to those depicted in FIG. 1B. The value 20 T of the steady-state induced displacement was extrapolated from each curve 20, and the extrapolated displacement values were then normalized by their corresponding PRF and combined to form a relative compliance curve 30.

Figure 8:
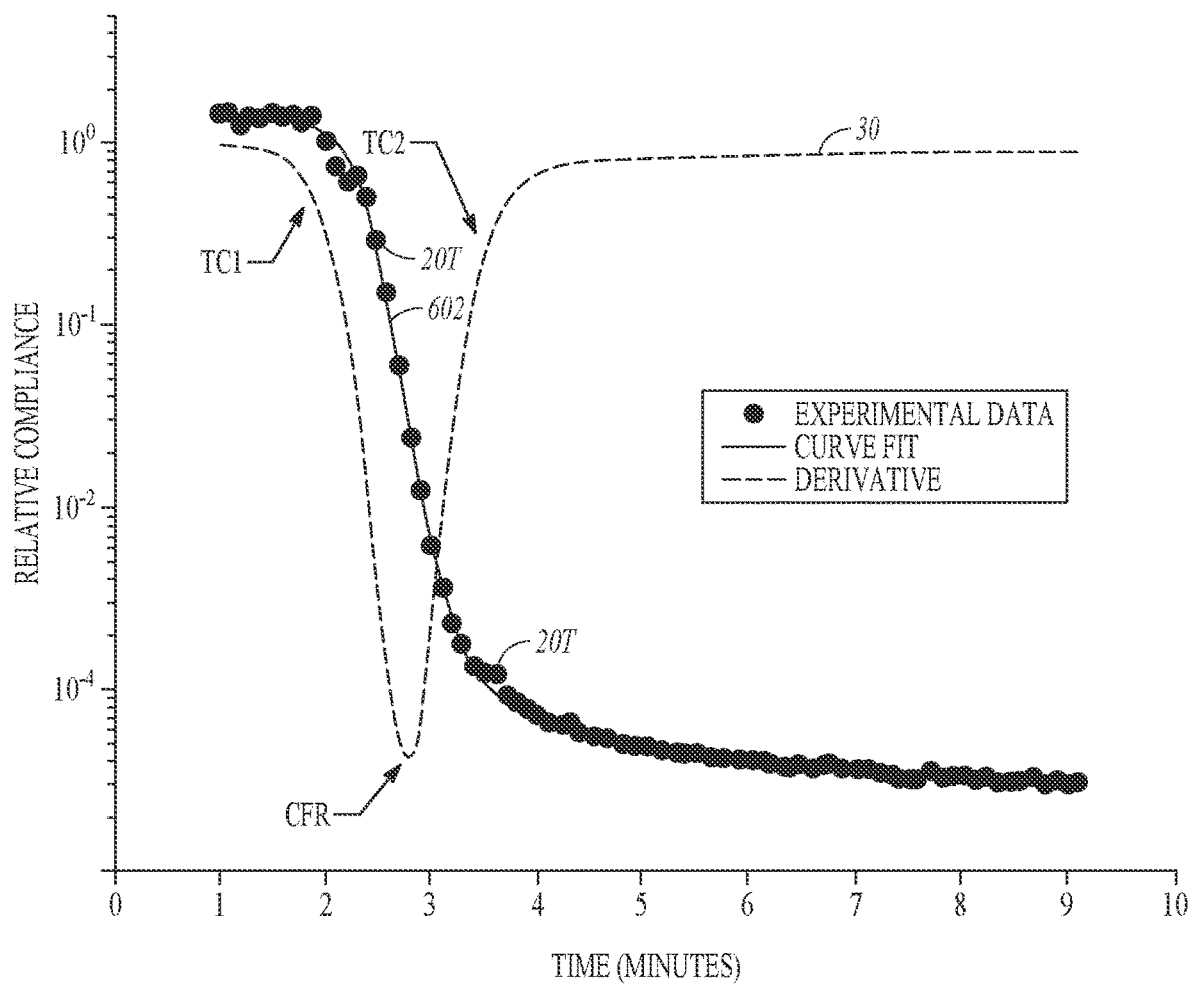
FIG. 8 graphically illustrates sonorheometry parameters that were calculated by fitting values to a sigmoidal curve and evaluating the first derivative of the curve according to an embodiment of the present invention.

The sonorheometry parameters were calculated by fitting values 20 T to a sigmoidal curve 602 and evaluating the first derivative 30 of the curve 602, as shown in FIG. 8. For example, the clotting times $TC_1$ and $TC_2$ were calculated based on a threshold value of the derivative curve (20% of the minimum value), whereas the clotting slope CFR is the minimum of the derivative curve. In the results presented here, the stiffness $S_{MAX}$ was estimated using the value of the relative compliance three minutes after $TC_2$. Identical methods and parameters were calculated for the fibrinolytic process.

Statistical analysis was performed in MATLAB. An unpaired, two-tailed t-test was used to assess the significance of the differences observed in sonorheometry parameters. In all instances, a P-value<0.05 was considered significant.

Results

Assessment of Coagulation Plasma Factors and Fibrin Polymerization

Figure 9A:
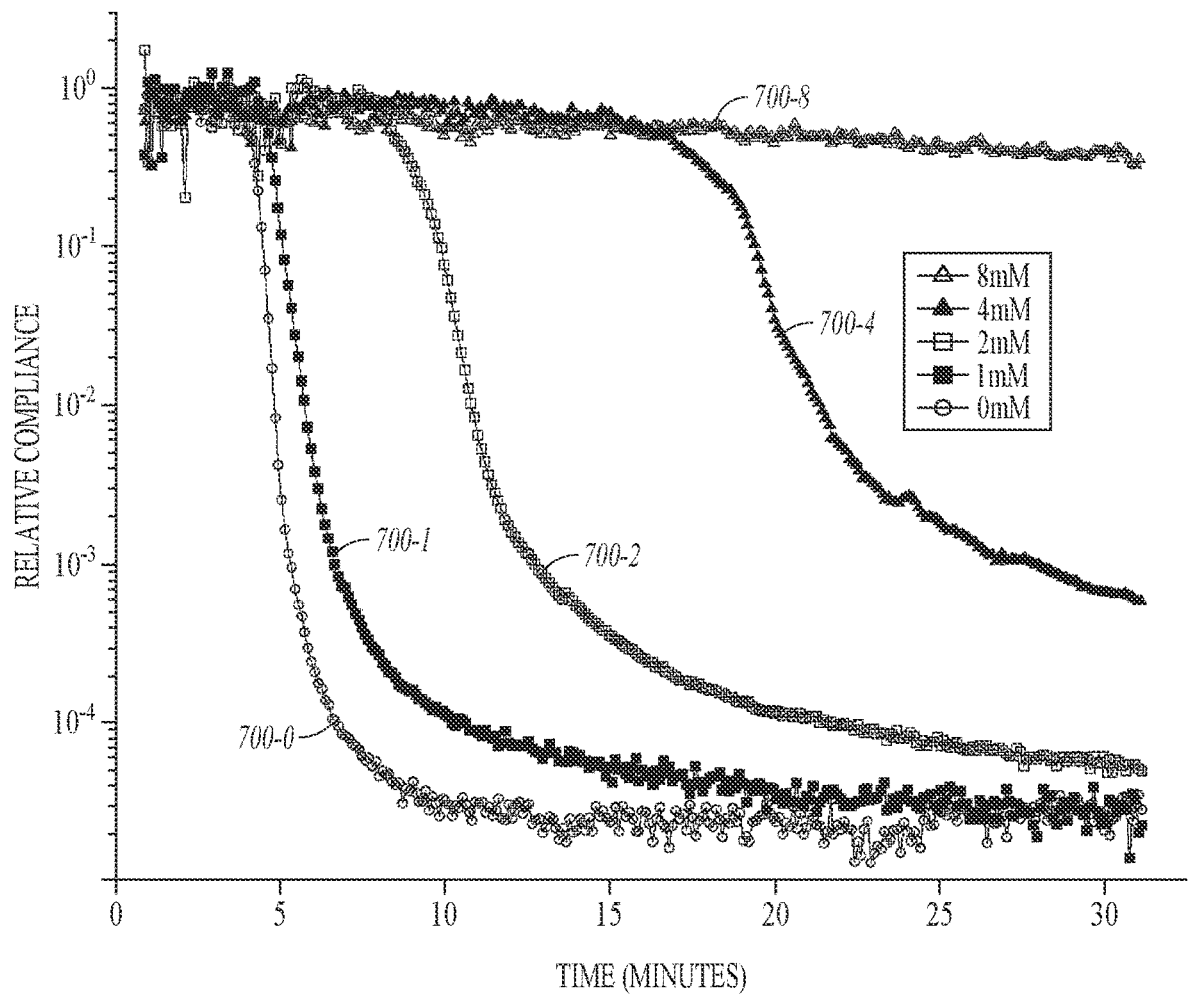
FIG. 9A shows sonorheometry curves indicating that increasing concentrations of GPRP produced distinctive changes in mechanical properties.
Figure 9B:
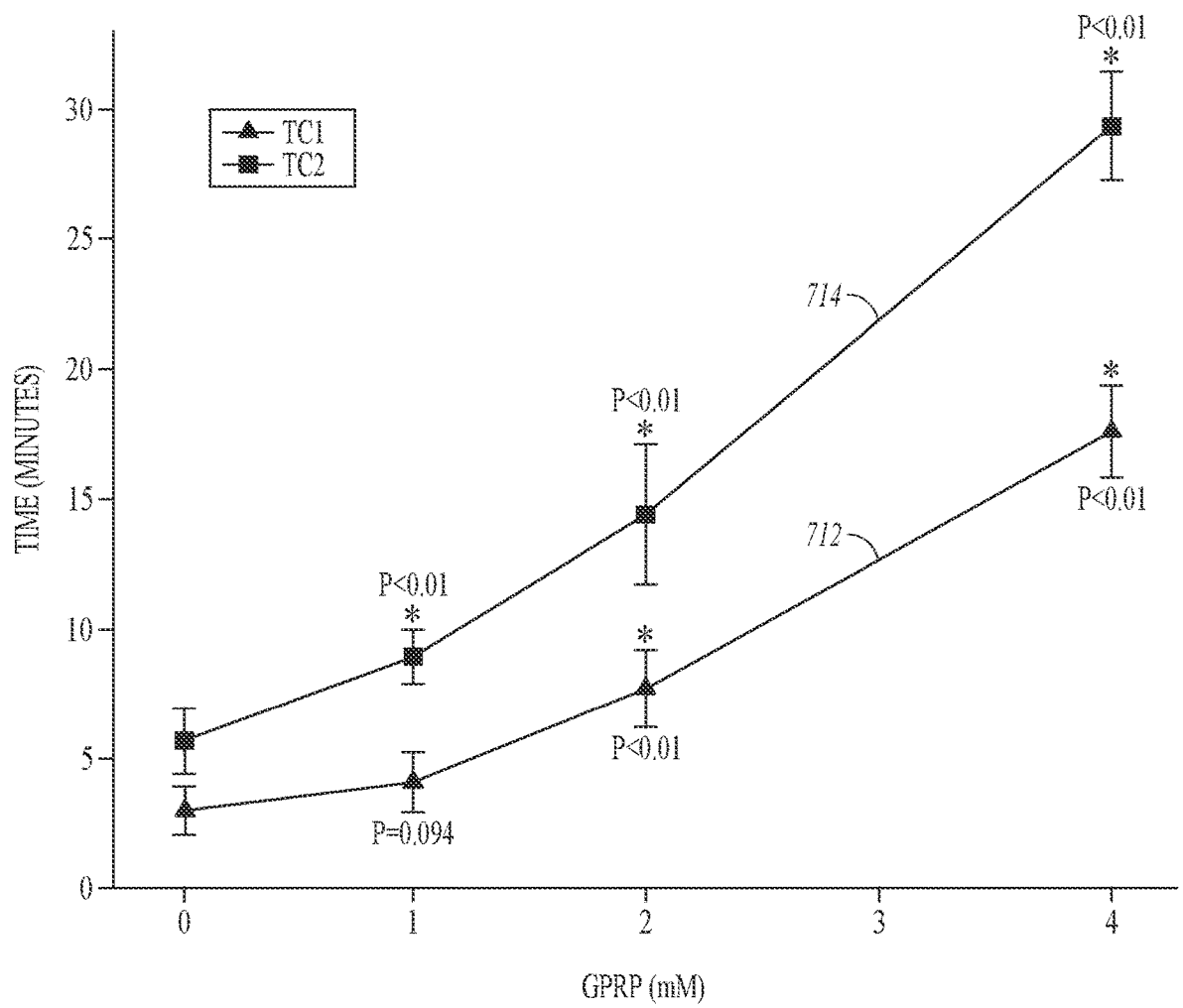
FIG. 9B shows plots illustrating increase of initial and final clotting times $TC_1$ and $TC_2$ with an increase in the concentration of GPRP added to the sample.
Figure 9C:
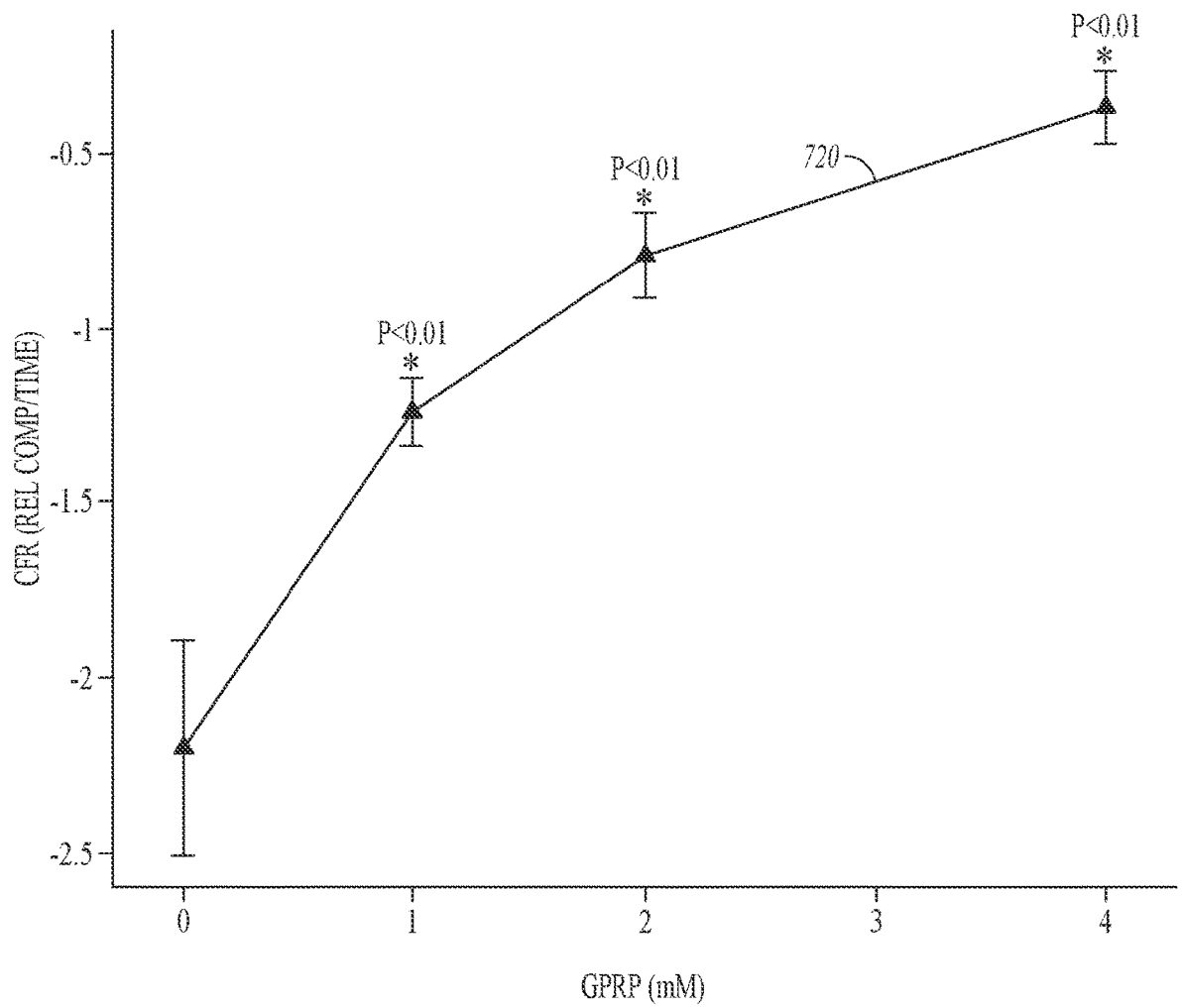
FIG. 9C illustrates significant changes that were observed for the clot formation rate CFR with increasing concentrations of GPRP added to the sample.
Figure 9D:
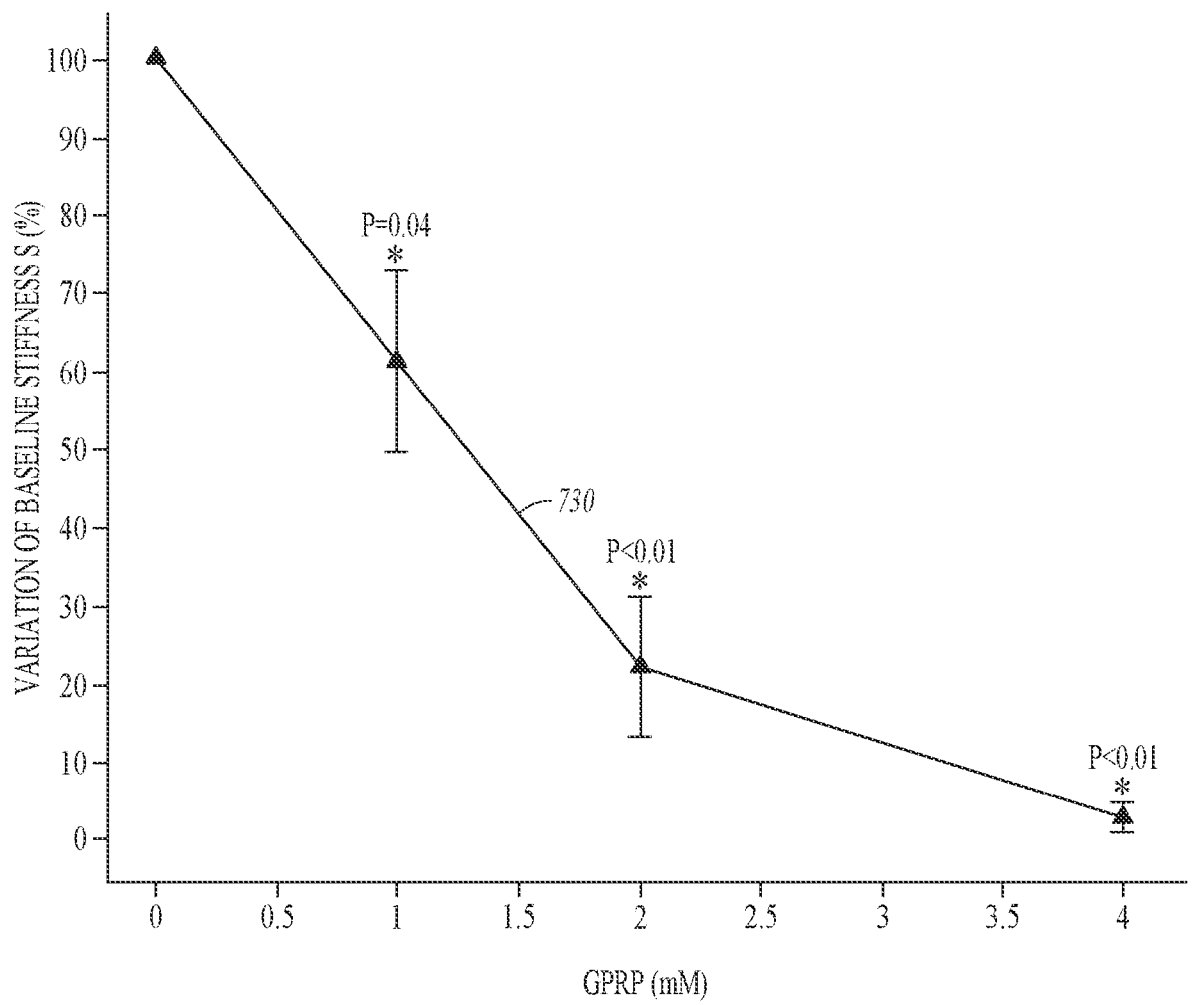
FIG. 9D illustrates significant changes in the stiffness S of the sample with increases in the concentration of GPRP.

These experiments were performed to characterize the function of the plasma coagulation factors and the consequent generation of a viscoelastic fibrin structure using sonorheometry. Fibrin is the building block of blood clots. Blood samples from 5 volunteers were obtained and the Gly-Pro-Arg-Pro (GPRP) peptide was added in titrated quantities to achieve final concentrations of 0, 1, 2, 4, and 8 mM. GPRP is a strong inhibitor of fibrin polymerization that blocks the sites located in the γ chains at the two D end domains of the fibrinogen molecule, as described in further detail by Laudano et al., Studies on synthetic peptides that bind to fibrinogen and prevent fibrin polymerization. Structural requirements, number of binding sites, and species differences. Biochem 1980; 19:1013-1019, which is hereby incorporated herein, in its entirety, by reference thereto. Increasing concentrations of GPRP produced distinctive changes in mechanical properties, as shown in the sonorheometry compliance curves 700-0, 700-1, 700-2, 700-4 and 700-8 in FIG. 9A, which correspond to GPRP concentrations of 0, 1, 2, 4, and 8 mM, respectively. FIG. 9B shows an exemplary set of sonorheometry curves obtained from a single volunteer. Both initial and final clotting times $TC_1$ and $TC_2$ increase with the concentration of GPRP, as noted in Chakroun et al, "The influence of fibrin polymerization and platelet-mediated contractile forces on citrated whole blood thromboelastography profile". Thromb. Haemost. 2006; 95:822-828 and in Laudano et al, "Synthetic peptide derivatives that bind to fibrinogen and prevent the polymerization of fibrin monomers". Proc. Natl. Acad. Sci. USA 1978; 75:3085-3089; both of which are hereby incorporated herein, in their entireties, by reference thereto. This was confirmed in the results, as shown by the clotting time curves 712 and 714 for $TC_1$ and $TC_2$, see FIG. 9B. These results suggest that $TC_1$ and $TC_2$ are representative of the beginning and ending phases of fibrin polymerization caused by the coagulation factors in the plasma. Significant changes were also observed for both the clot formation rate CFR (see curve 720 in FIG. 9C and the stiffness S (see curve 730 in FIG. 9D) with increases in the concentration of GPRP. The slope of CFR curve 720 is representative of the rate of fibrin polymerization. As expected, the process of fibrin polymerization was a key component in determining the dynamics of clot formation and clot stiffness. Increasing levels of GPRP decreased both the rate of fibrin polymerization and the final stiffness of the formed clot.

Assessment of Platelet Function

Figure 10A:
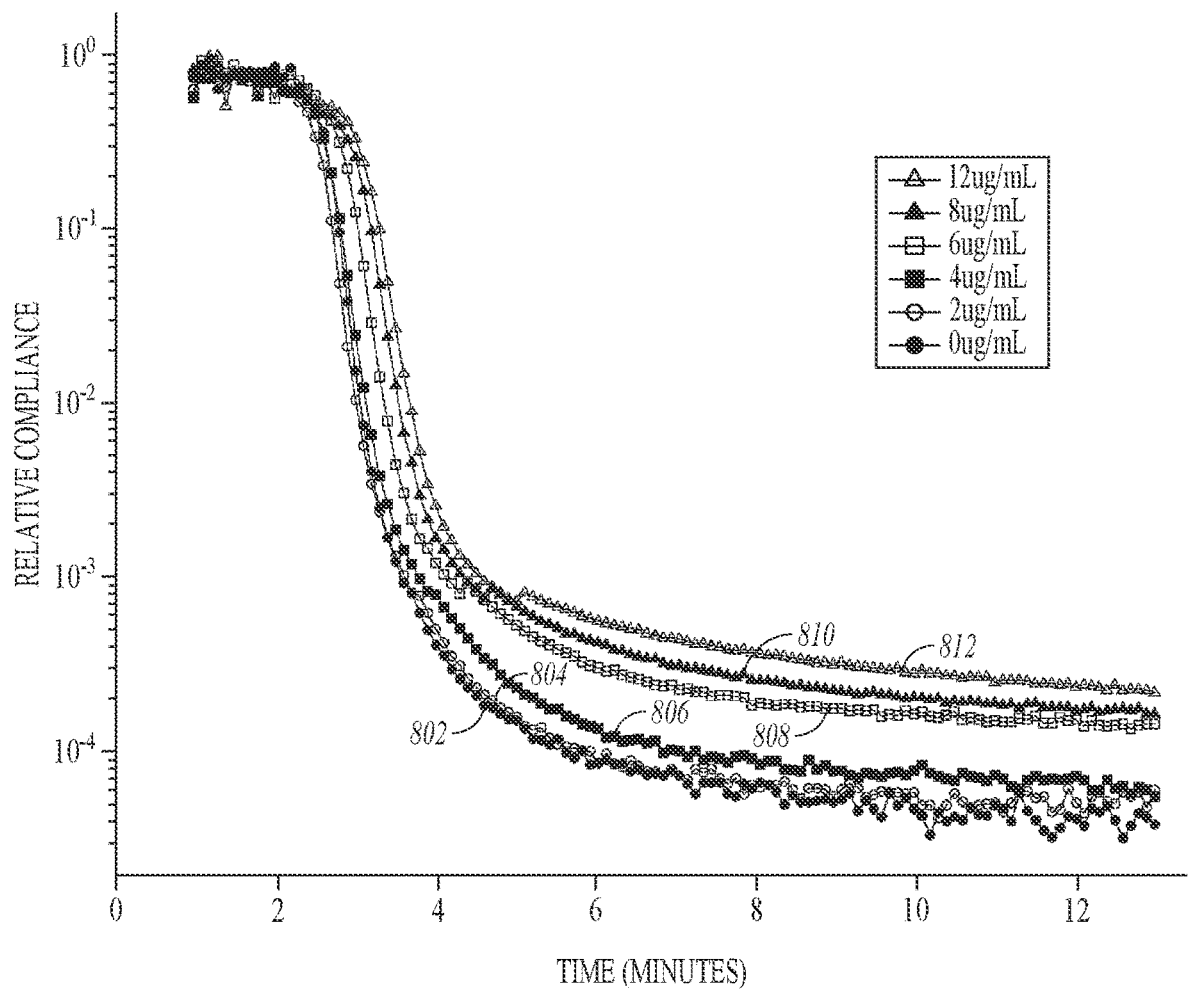
FIG. 10A shows graphical results illustrating that increasing inhibition of platelet aggregation reduces the stiffness $S_{MAX}$ yielding a softer clot.
Figure 10B:
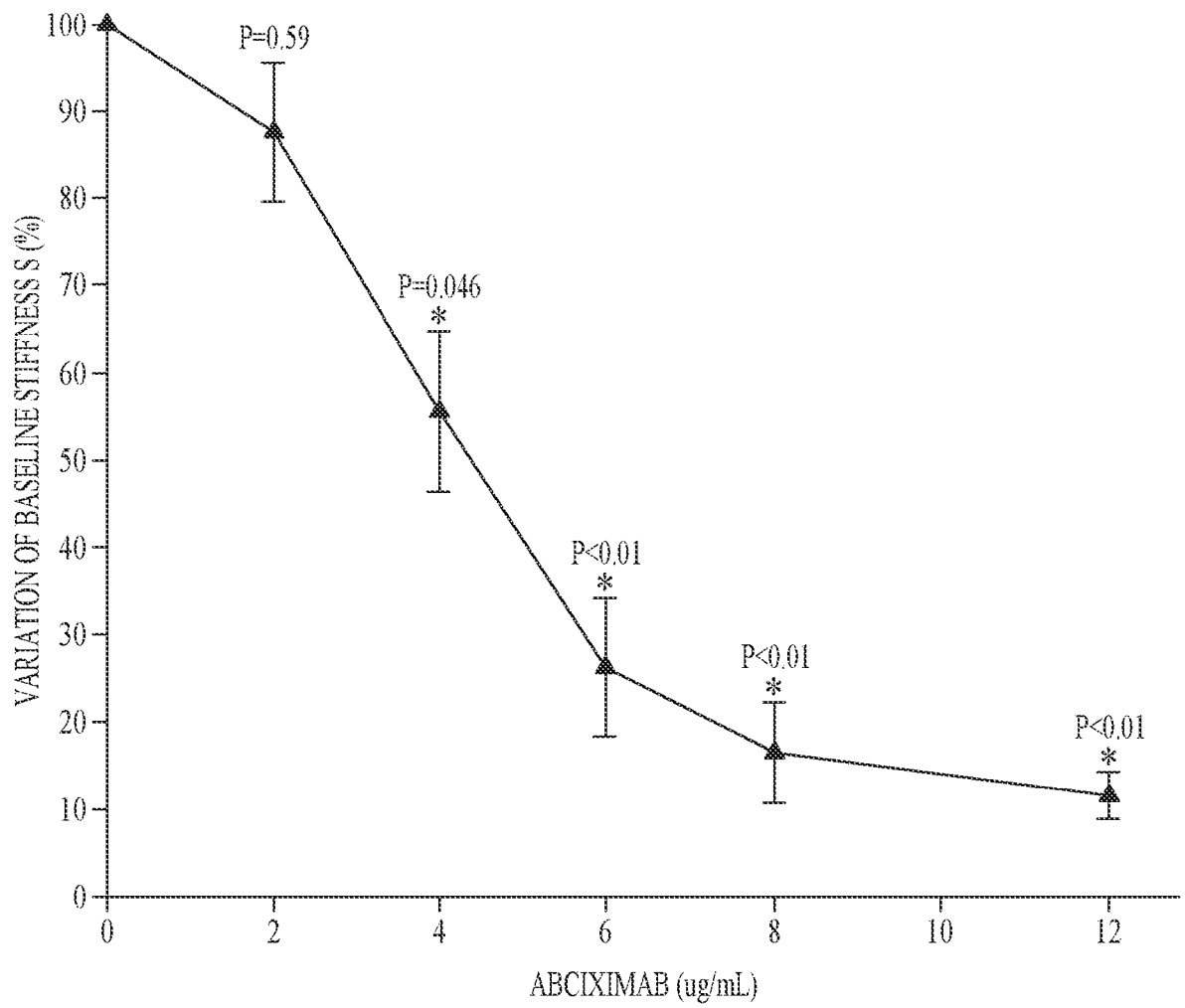
FIG. 10B shows percentage changes in $S_{MAX}$ as a function of abciximab concentration according to an embodiment of the present invention.

Platelets play various important roles during hemostasis. These complex functions include: adhesion to the site of injury, activation and shape change, secretion of internal granules to recruit additional platelets, aggregation with surrounding platelets via fibrinogen links, interaction with fibrin mesh, and clot retraction in order to reduce the volume of the clot, see also Carr, "In Vitro Assessment of Platelet Function", Trans. Med. Review 1997; 11:106-115 and Packham, "Role of platelets in thrombosis and hemostasis, "Can. J. Physiol. Pharmacol. 1994; 72:278-284; both of which are hereby incorporated herein, in their entireties, by reference thereto. Of particular importance is the mechanism of aggregation, which ultimately determines the ability to form a platelet plug that can stop bleeding. Aggregation is mediated by fibrinogen that binds to the glycoprotein (GP) IIb/IIIa, forming bridges between adjacent activated platelets. Experiments were performed to investigate the contribution of platelets on sonorheometry measurements. Titrated quantities of monoclonal antibody abciximab were added to blood samples from five individuals to achieve final concentrations of 0, 2, 4, 6, 8, and 12 µg/ml. Abciximab is a potent inhibitor of platelet aggregation that prevents platelets from binding to fibrinogen by blocking the IIb/IIIa receptor on the platelet's surface, see The EPIC Investigators, "Use of monoclonal antibody directed against the platelet glycoprotein IIb/IIIa receptor in high-risk coronary angioplasty", N. Engl. J. Med. 1994; 330:956-961 and Collier et al., "A murine monoclonal antibody that completely blocks the binding of fibrinogen to platelets produces a thromastenic-like state in normal platelets and binds to glycoproteins IIb and/or IIIa", J. Clin. Invest. 1983; 72:325-338, both of which are hereby incorporated herein, in their entireties, by reference thereto. The resulting sonorheometry curves demonstrate that increasing inhibition of platelet aggregation reduces the stiffness $S_{MAX}$ yielding a softer clot, as shown by curves 802, 804, 806, 808, 810 and 812 in FIG. 10A, which correspond to concentrations of abciximab in the samples of 0, 2, 4, 6, 8, and 12 µg/ml, respectively. The other parameters describing the dynamics of clot formation and dissolution did not change significantly, but fell within the variability of system 100. Final clot stiffness varied by over one order of magnitude across the concentrations used for this experiment. FIG. 10B shows percentage changes in $S_{MAX}$ as a function of abciximab concentration.

The results of the experiments and plots shown in FIGS. 9A-10B suggest that the final stiffness of the clot resulted from the interaction of aggregated platelets and fibrin network. The stiffness parameter $S_{MAX}$ is thus indicative of the combined mechanical functions of the fibrin network and the platelet aggregation/contractile function. The ability of sonorheometry to characterize platelet aggregation is thus useful, for example, to determine the efficacy of therapies based on Plavix® or non-steroidal anti-inflammatory drugs (NSAIDs) and to discriminate responders from non-responders to these drugs.

Assessment of Fibrinolytic Proteins

Experiments were performed to assess fibrinolysis using sonorheometry. For this set of experiments, titrated amounts of urokinase type plasminogen activator were added to the samples. Urokinase type plasminogen activator is a serine protease that promotes dissolution of the fibrin network that forms the blood clot, see Lijnen et al., "The mechanism of plasminogen activation and fibrin dissolution by single chain urokinase-type plasminogen activator in a plasma milieu in vitro", Blood 1989; 73:1864-1872, which is hereby incorporated herein, in its entirety, by reference thereto. Total amounts of urokinase were 0, 100, 150, and 200 Units per ml of blood, respectively. Urokinase shows significant effects on the measurements performed by sonorheometry, as indicated by the relative compliance curves 902, 904, 906 and 908 that correspond to total amounts of urokinase of 0, 100, 150 and 200 Units per ml of blood sample, respectively. The blood samples returned to a viscous fluid significantly faster with increasing concentrations of urokinase, as expected. Both clot lysis times $TL_1$ and $TL_2$ decreased as a function of urokinase concentration, as illustrated by the curves 912 and 914 (corresponding to $TL_1$ and $TL_2$, respectively) in FIG. 110B.

Figure 11A:
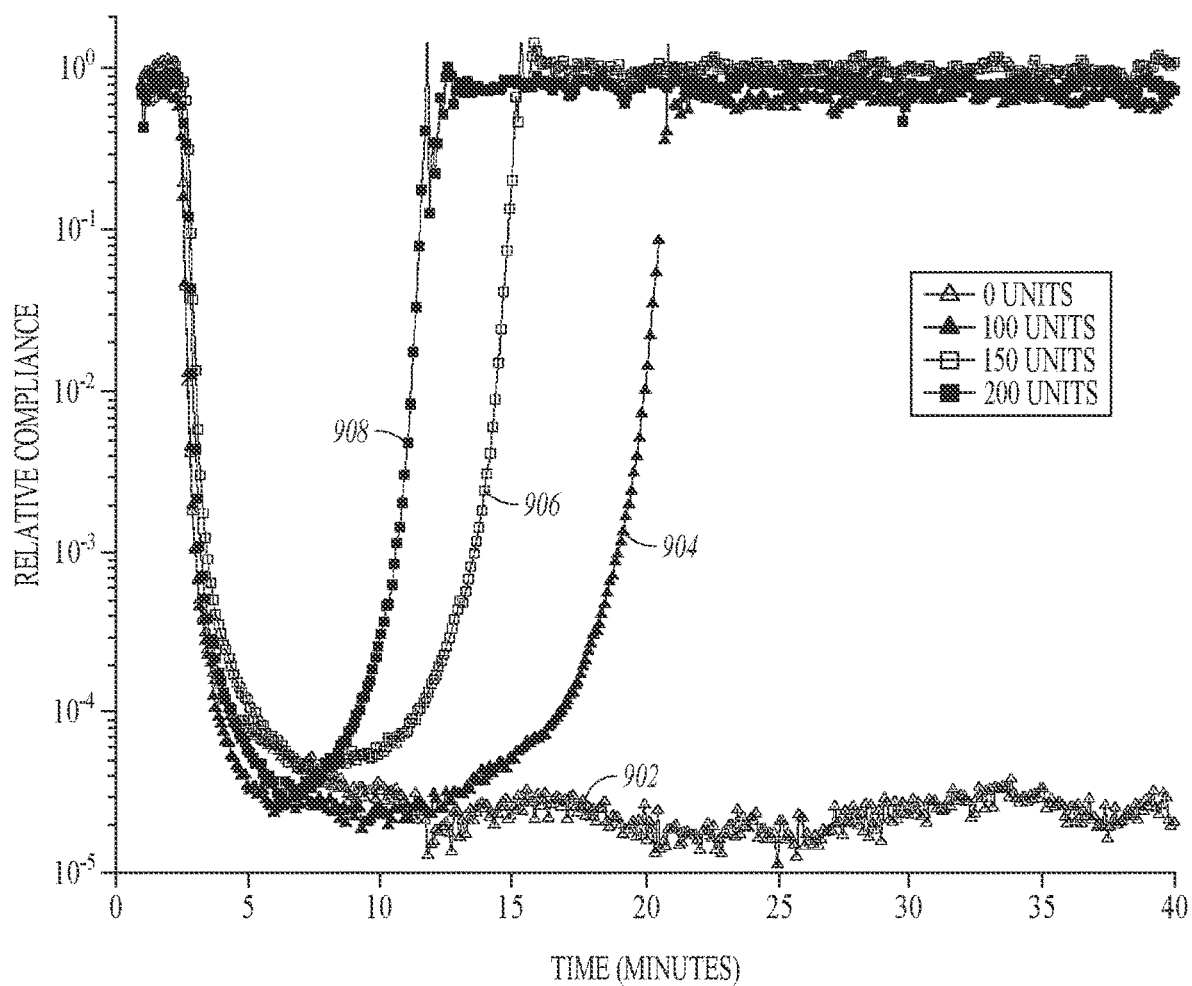
FIGS. 11A-11B show that the increased fibrinolytic activity caused by urokinase rapidly dissolved the blood clot and restored the original mechanical conditions prior to clot formation.
Figure 11B:
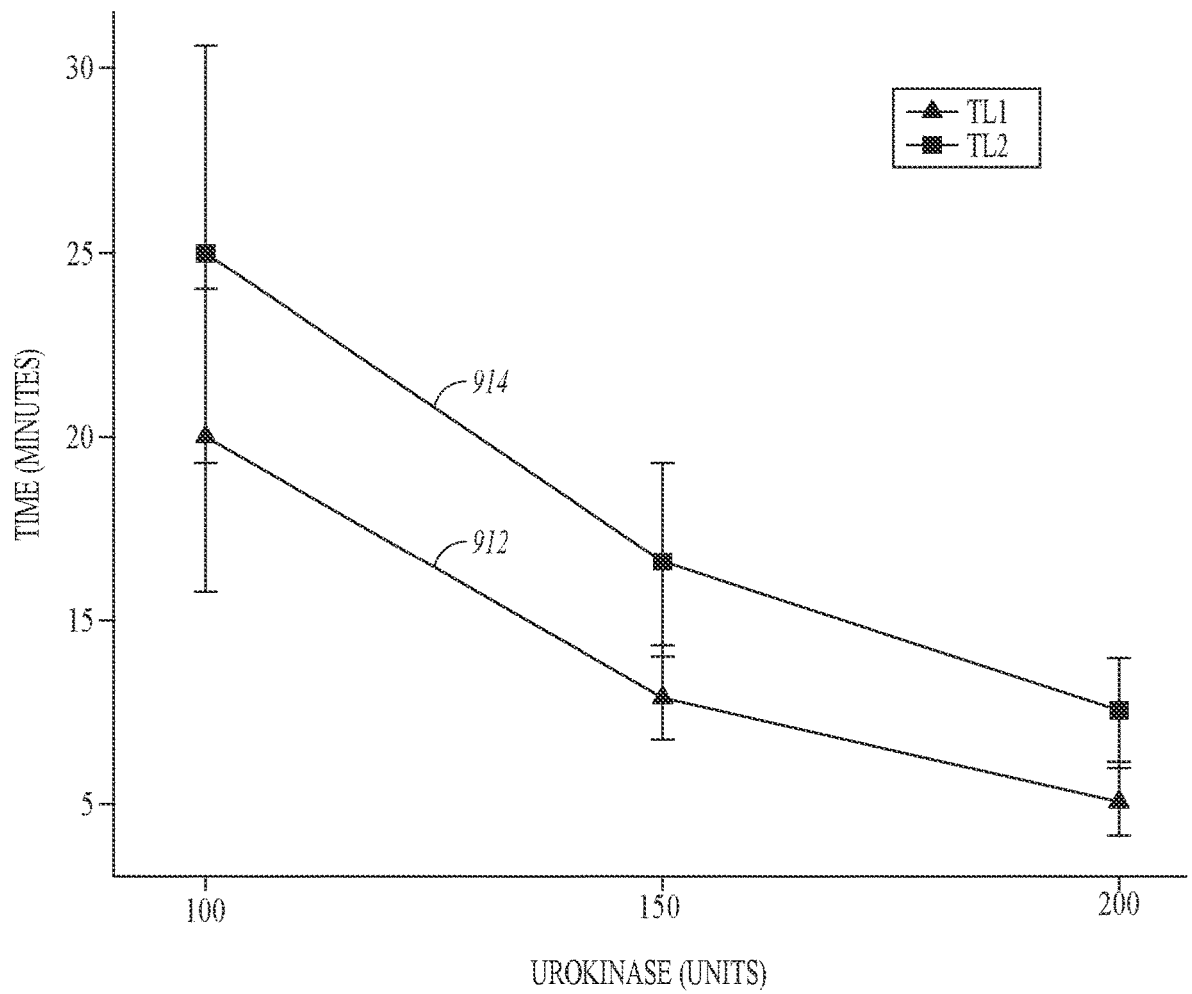

FIGS. 11A-11B show that the increased fibrinolytic activity caused by urokinase rapidly dissolved the blood clot and restored the original mechanical conditions prior to clot formation. The results in FIGS. 11A-11B suggest that the parameters $TL_1$ and $TL_2$ can be used to characterize dysfunctions of the fibrinolytic system, such as in the case of hyperfibrinolysis.

Application of sonorheometry according to the present invention requires neither moving mechanical parts nor direct contact with the sample and viscoelasticity measurements can be performed with minimal mechanical strain on the blood. The shear strains generated by the acoustic radiation force are kept below 3%, which is within the linear range of blood (the shear levels were also confirmed by simulations using finite element models). Furthermore, sonorheometry can be implemented with compact, readily available off-the-shelf electronic components. The use of smaller blood samples, such as those that might be obtained through a finger-stick, could be achieved by increasing the center frequency of the ultrasound pulses used to generate acoustic radiation force. Higher frequencies not only reduce the dimensions of the ultrasound beam, but also increase attenuation within the blood sample, which increases the magnitude of the applied acoustic radiation force, see Szabo, "Diagnostic Ultrasound Imaging, Academy Press, 2004, which is hereby incorporated herein, in its entirety, by reference thereto.

Sonorheometry holds great potential to improve patient diagnosis and treatment in a variety of clinical scenarios. By utilizing different activators, blocking agents, and other reagents, sonorheometry can provide a highly versatile platform for (i) screening for increased bleeding or clotting risks, (ii) guiding patient care in a variety of clinical settings, and/or (iii) discovering fundamental clotting/bleeding mechanisms. This is of great importance since thrombotic and hemorrhagic diseases represent the leading cause of mortality and morbidity in the developed world. According to one embodiment, the present invention can guide transfusions of blood products during emergency or surgical procedures. While transfusions of blood products have had a significant impact in saving millions of lives, blood is a scarce resource and usage must be carefully optimized. Furthermore, several concerns still exist regarding the safety of transfusion therapies, which carry risks of infection and immune response. Current transfusion guidelines are rarely implemented in clinical practice due to the limitations of current technology. Because of these limitations, the clinical state of the art in most institutions is iterative transfusion and subjective evaluation of bleeding. This process is slow and prone to over-transfusion. According to an embodiment of the present invention, sonorheometry can be used to quantify the hemostatic system at the patient's bedside and inform targeted use of blood products, thus minimizing unnecessary transfusions, speeding treatment, and improving patient outcomes.

As shown and described above, the present invention can assess the function of coagulation factors, platelets, and fibrinolytic proteins in whole blood. In an alternative embodiment, the use of a second ultrasound transducer can be used at the opposite end of the blood sample under analysis to estimate variation in acoustic properties through the sample. This allows determination of the absolute value of the viscoelastic parameters (rather than indirect relative parameters).

Reproducibility Error of Repeated Sonorheometry Measurements

The intrinsic variability of sonorheometry was tested using whole blood samples from five volunteers. For each subject, ten samples were obtained into 1.8 ml Vacutainers (with 3.2% sodium citrate) and analyzed sequentially using kaolin activation. The estimated coefficients of variation were below 6% (averages over the five subjects) for all of the parameters described above, except $LT_1$ and $LT_2$ (the coefficient of variation for $LT_1$ and $LT_2$ were not estimated since clot lysis was not observed within the experiment time of fifteen minutes).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of evaluating a mechanical property of a sample by adjusting a characteristic of a force applied to the sample, the method comprising using a processor circuit configured or programmed to control a force applicator and to monitor sensor, the method comprising:
   using the processor circuit to control the force applicator to apply a force to the sample sufficient to physically displace a portion of the sample using the force applicator;
   using the processor circuit to monitor the sensor to measure a strain of the sample in response to the applied force;
   using the processor circuit to control the force applicator to adjust a characteristic of the force applied to the sample in response to a measured strain being outside a predetermined range of strain values, wherein the adjusted characteristic is increased or decreased to adjust an induced displacement depending upon whether the measured strain is below or above the predetermined range, respectively; and
   using the processor circuit to compute a mechanical property value of the sample resultant from the measured strain of the sample;
   wherein the predetermined range includes an upper threshold determined at least to avoid mechanical damage to the sample when the measured strain is below the upper threshold
   wherein the force applicator comprises a drive configured to apply a torque to the sample relative to a pin comprising the sensor or the force applicator comprises an ultrasonic transducer coupled to a probe, the probe configured to mechanically contact the sample and configured to oscillate at a resonant frequency that varies in relation to a viscoelastic property of the sample.

2. The method of claim 1, wherein using the processor circuit to control the force applicator to apply the force to the sample includes using the processor circuit to control the force applicator to direct a series of acoustic pulses into the sample to physically displace a portion of the sample, wherein the measuring the strain includes estimating the strain of the sample using sensed echoes returned from a portion of sample in response to at least a portion of the series of acoustic pulses.

3. The method of claim 1, comprising:
using the processor circuit to control the force applicator to iteratively apply an adjusted force, using the processor circuit to monitor the sensor to measure the strain of the sample in response to the iteratively applied force, and using the processor circuit to control the force applicator to adjust the applied force in response to the measured strain; and
computing the mechanical property value of the sample in response to the iterative application of the adjusted force and resulting from the measured strain.

4. The method of claim 3, wherein the mechanical property value is a value of a time-dependent mechanical property.

5. The method of claim 4, wherein the sample comprises blood, and wherein the method comprises:
computing a series of mechanical property values in response to the iterative application of the adjusted force and resulting from the measured strain; and
computing a hemostatic characteristic curve from the mechanical property values.

6. The method of claim 1, wherein the mechanical property comprises a viscoelastic property of the sample.

7. The method of claim 6, wherein the viscoelastic property includes one or more of an absolute stiffness or a relative stiffness of the sample.

8. A system for evaluating a mechanical property of a sample by adjusting a characteristic of a force applied to the sample, the system comprising:
a force applicator configured to apply a force to the sample sufficient to physically displace a portion of the sample;
a sensor configured to measure a strain of the sample in response to the applied force;
a processor configured to:
control the force applicator to adjust a characteristic of the force applied to the sample by the force applicator in response to a measured strain being outside a predetermined range of strain values, wherein the adjusted characteristic is increased or decreased to adjust an induced strain depending upon whether the measured strain is below or above the predetermined range, respectively; and
compute a mechanical property value of the sample resultant from the measured strain of the sample;
wherein the predetermined range includes an upper threshold determined at least to avoid mechanical damage to the sample when the measured strain is below the upper threshold;
wherein the force applicator comprises a drive configured to apply a torque to the sample relative to a pin comprising the sensor or the force applicator comprises an ultrasonic transducer coupled to a probe, the probe configured to mechanically contact the sample and configured to oscillate at a resonant frequency that varies in relation to a viscoelastic property of the sample.

9. The system of claim 8, wherein the force applicator includes at least one acoustic transducer configured to direct a series of acoustic pulses into the sample to physically displace a portion of the sample, wherein the sensor is configured to estimate the strain of the sample using echoes returned from a portion of sample in response to at least a portion of the series of acoustic pulses.

10. The system of claim 8, wherein the processor is configured to:
iteratively apply an adjusted force, measure strain of the sample in response to the iteratively applied force, and adjust the applied force in response to the measured strain; and
compute the mechanical property value of the sample in response to the iterative application of the adjusted force and resulting from the measured strain.

11. The system of claim 10, wherein the mechanical property value is a value of a time-dependent mechanical property.

12. The system of claim 11, wherein the sample comprises blood, and wherein the processor is configured to:
compute a series of mechanical property values in response to the iterative application of the adjusted force and resulting from the measured strain; and
compute a hemostatic characteristic curve from the mechanical property values.

13. The system of claim 8, wherein the mechanical property comprises a viscoelastic property of the sample.

14. The system of claim 13, wherein the viscoelastic property includes one or more of an absolute stiffness or a relative stiffness of the sample.

15. The system of claim 8, wherein the upper threshold corresponds to a specified strain limit.

16. The system of claim 8, wherein the predetermined range comprises a lower threshold corresponding to a noise threshold for the strain measurement.

17. The system of claim 8, wherein the characteristic of the force comprises a magnitude of the force.

18. The system of claim 8, wherein the characteristic of the force comprises a repetition frequency of pulses included in the applied force.

19. The system of claim 8, wherein the force applicator comprises a drive configured to apply a torque to the sample relative to a pin; and
wherein the sensor includes the pin.

20. The system of claim 8, wherein the force applicator comprises a transducer coupled to a probe, the probe configured to mechanically contact the sample and configured to oscillate at a resonant frequency that varies in relation to a viscoelastic property of the sample.

21. The method of claim 1, wherein the force applicator comprises a drive configured to apply a torque to the sample relative to a pin comprising the sensor.

22. The method of claim 1, wherein the force applicator comprises an ultrasonic transducer coupled to a probe, the probe configured to mechanically contact the sample and configured to oscillate at a resonant frequency that varies in relation to a viscoelastic property of the sample.

* * * * *